(12) United States Patent
Lin et al.

(10) Patent No.: US 6,727,232 B2
(45) Date of Patent: Apr. 27, 2004

(54) NUCLEOSIDE PEPTIDE ANTIBIOTICS OF AA-896

(75) Inventors: Yang-I Lin, Tappan, NY (US); Zhong Li, Congers, NY (US); Gerardo DelaCruz Francisco, Orangeburg, NY (US); Leonard Alexander McDonald, Mountainside, NJ (US)

(73) Assignee: Wyeth Holdings Corporation, Madison, NJ (US)

( * ) Notice: Subject to any disclaimer, the term of this patent is extended or adjusted under 35 U.S.C. 154(b) by 22 days.

(21) Appl. No.: 10/131,939

(22) Filed: Apr. 25, 2002

(65) Prior Publication Data

US 2003/0054983 A1 Mar. 20, 2003

Related U.S. Application Data

(60) Provisional application No. 60/286,401, filed on Apr. 25, 2001, provisional application No. 60/290,139, filed on May 10, 2001, provisional application No. 60/286,297, filed on Apr. 25, 2001, provisional application No. 60/290,140, filed on May 10, 2001, provisional application No. 60/286,402, filed on Apr. 25, 2001, and provisional application No. 60/290,156, filed on May 10, 2001.

(51) Int. Cl.[7] .......................... A01N 43/04; A61K 31/70
(52) U.S. Cl. ............................ 514/50; 514/43; 514/49; 536/22.1; 536/28.1; 536/28.4; 536/28.53; 536/55.3
(58) Field of Search .............................. 514/43, 49, 50; 536/22.1, 28.1, 28.4, 28.53, 55.3

(56) References Cited

FOREIGN PATENT DOCUMENTS

| JP | 5078385 | 3/1993 |
|---|---|---|
| JP | 05078385 | 3/1993 |

OTHER PUBLICATIONS

Isono, K; Uramoto, M; Kusakabe, H.; Kimura, K.; Izaki, K.; Nelson, C.C.; McCloskey, J.A.; J. Antibiotics, 1985, 38, 1617–1621.
Ubukata, M.; Isono, K.; Kimura, K.; Nelson, C.C.; McCloskey, J.A.; J. Am.Chem.Soc., 1988, 110, 4416–4417.
Kimura, K.; Miyata, N.; Kawanishi, G.; Kamino, Y.; Izaki, K.; Isono, K.; Agric.Biol.Chem., 1989, 53, 1811–1815.
Kimura, K.; Ikeda, Y.; Kagami, S.; Yoshihara, M.; J. Antibiotics, 1998, 51, 1099–1104.
Ubukata, M.; Kimura, K.; Isono, K.; Nelson, C.C.; Gregson, J.M.; McClosky, J.A.; J. Org.Chem., 1992, 57, 6392–6403.
Mengin–Lecreaulz, et al.; J. Bacteriol 173(15); 1991; 4625–4636.
M. Heravi, et al.; Monatsh. Chem.; 1998, 129(12), 1305–1308.
Dini, C.; Drochon, N.; Guillot, J.C.; Mauvais, P.; Walter, P.; Aszodi, J.; Synthesis of Analogues of the O–β–D–Ribofuranosyl Nucleoside Moiety of Liposidomycins. Part 2: Role of the Hydroxyl Groups upon the Inhibition of MraY; Biorganic & Medicinal Chemistry Letters 11; 2001; pp. 533–536.
Dini, C.; Collette, P.; Drochon, N.; Guillot, J.C.; Lemoine, G.; Mauvais, P.; Aszodi, J.; Synthesis of the Nucleoside Moiety of Liposidomycins: Elucidation of the Pharmacophore of this Family of MraY Inhibitors; Biorganic & Medicinal Chemistry Letters 10; 2000; pp. 1839–1841.
PCT/US02/13024 International Search Report mailed Aug. 20, 2002.

*Primary Examiner*—Patrick Lewis
(74) *Attorney, Agent, or Firm*—Daniel B. Moran

(57) ABSTRACT

This invention relates to antibiotic compounds AA896 of the formula

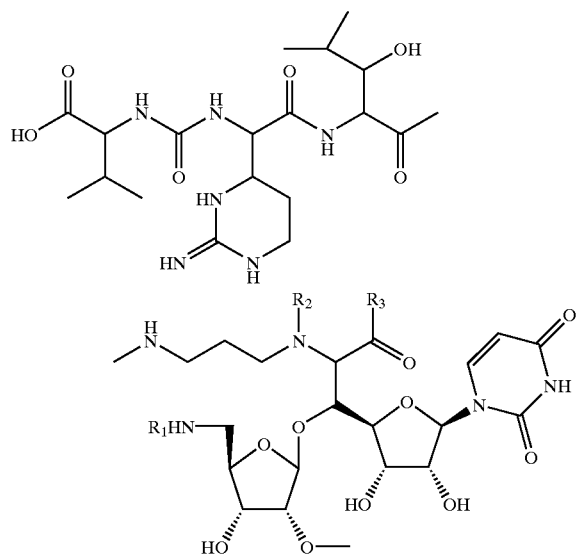

wherein:

$R_1$ is H, aryl, alkyl ($C_1$–$C_{20}$), —$CH_2$-aryl, —C(O)alkyl ($C_1$–$C_{20}$), —C(O)NHalkyl($C_1$–$C_{20}$), or —C(O)NHaryl;

$R_2$ is H, alkyl ($C_1$–$C_{20}$), —$CH_2$aryl, alkyl ($C_1$–$C_{20}$) or —C(O)alkyl($C_1$–$C_{20}$);

$R_3$ is —OH;

$R_2$ and $R_3$ may optionally be taken together to form a moiety

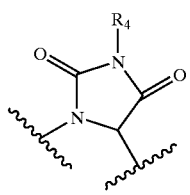

$R_4$ is alkyl ($C_1$–$C_{20}$), or aryl;

or a pharmaceutically acceptable salt thereof.

31 Claims, 17 Drawing Sheets

NUCLEOSIDE PEPTIDE ANTIBIOTICS OF AA-896

CROSS REFERENCE TO RELATED APPLICATIONS

"This application claims priority from copending provisional applications Serial No. 60/286,401 filed on Apr. 25, 2001, Serial No. 60/290,139, filed on May 10, 2001, Serial No. 60/286,297 filed Apr. 25, 2001, Serial No. 60/290,140 filed May 10, 2001, Serial No. 60/286,402 filed Apr. 25, 2001 and Serial No. 60/290,156 filed May 10, 2001 the entire disclosures of which are hereby incorporated by reference."

FIELD OF THE INVENTION

The present invention relates to novel compounds of AA-896 which exhibit antibacterial activity.

BACKGROUND OF THE INVENTION

Natural products, Liposidomycins A, B and C, have been isolated and reported to have antibacterial activity(Isono, K.; Uramoto, M.; Kusakabe, H.; Kimura, K.; Izaki, K.; Nelson, C. C.; McCloskey, J. A.,*J.Antibiotics,* 1985, 38, 1617–1621. Ubukata, M.; Isono, K.; Kimura, K.; Nelson, C. C.; McCloskey, J. A. *J.Am.Chem.Soc.,* 1988,110, 4416–4417. Kimura, K.; Miyata, N.; Kawanishi, G.; Kamino, Y.; Izaki, K.; Isono, K. *Agric.Biol.Chem.,* 1989, 53,1811–1815.). Isolated Liposidomycins A-(I), A-(II), A-(III) and A-(IV) are also reported to have antibacterial activity (Kimura, K.; Ikeda, Y.; Kagami, S.; Yoshihara, M., *J. Antibiotics,* 1998, 51, 1099–1104. and other references herein). The detailed structural analysis of Liposidomycins A, B and C using their chemical degradation products has been reported (Ubukata, M.; Kimura, K.; Isono, K.; Nelson, C. C.; Gregson, J. M.; McClosky, J. A., *J.Org.Chem.,* 1992, 57, 6392–6403). Liposidomycin class compounds are further reported (JPO05078385) and are derivatives of 2-methylamino-3-(5-aminomethyl-4-hydroxy-3-hydroxy-tetrahydro-fura-2-yloxy)-3-[3,4-dihyoxy-5-(2,4-dioxo-3,4-dihydro-1 (2H)-pyrimidinyl)tetrahydro-2-furanyl]propanoic acid or the degraded products of 2-methylamino-3-(5-aminomethyl-4-hydroxy-3-hydroxy-tetrahydro-fura-2-yloxy)-3-[3,4-dihyoxy-5-(2,4-dioxo-3,4-dihydro-1 (2H)-pyrimidinyl) tetrahydro-2-furanyl]-propanoic acid.

This invention is concerned with a new series of nucleoside peptide antibiotics of AA-896.

SUMMARY OF THE INVENTION

This invention is concerned with novel nucleoside peptide antibiotics of AA-896 which have antibacterial activity; with methods of treating infectious disease in mammals employing these novel nucleoside peptide antibiotics; with pharmaceutical compositions containing these novel nucleoside peptide antibiotics and processes for the production of novel nucleoside peptide antibiotics of the invention. Compounds according to the invention comprise compounds of the formula

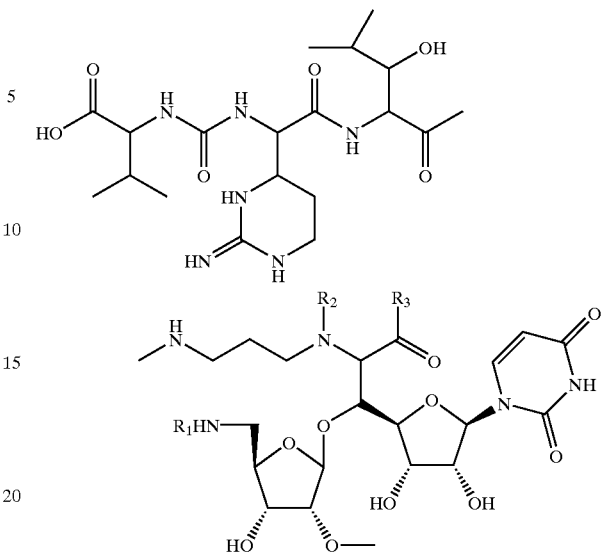

wherein:

$R_1$ is H, aryl, alkyl ($C_1$–$C_{20}$), —$CH_2$-aryl, —C(O)alkyl ($C_1$–$C_{20}$), C(O)NHalkyl($C_1$–$C_{20}$), or —C(O)NHaryl;

$R_2$ is H, alkyl ($C_1$–$C_{20}$), —$CH_2$aryl, or —C(O)alkyl ($C_1$–$C_{20}$);

$R_3$ is —OH;

$R_2$ and $R_3$ may optionally be taken together to form a moiety

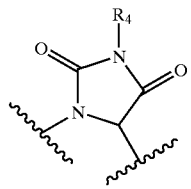

$R_4$ is alkyl ($C_1$–$C_{20}$), or aryl;

provided $R_1$ and $R_2$ are not H when $R_3$ is —OH or a pharmaceutically acceptable salt thereof.

Among the preferred groups of compounds of this invention including pharmaceutically acceptable salts thereof are those in the subgroups below, wherein other variables are as defined above:

a) $R_2$ and $R_3$ are taken together to form a moiety

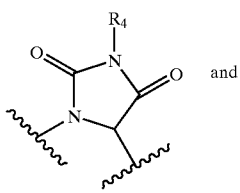

and b) $R_2$ is H, alkyl ($C_1$–$C_{12}$), or —$CH_2$aryl; and c) $R_1$ is H, —C(O)alkyl($C_1$–$C_{16}$), or —C(O)aryl when R₂ and R₃ are taken together to form a moiety

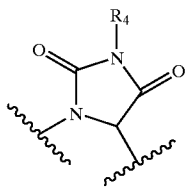

d) R₄ is alkyl(C₁–C₁₆), or aryl.

Specifically preferred compounds of the invention are the following compounds or a pharmaceutically acceptable salt thereof:

14-[5-((R)-{[(3R,4S,5R)-5-(Aminomethyl)-4-hydroxy-3-methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-3-(4-fluorophenyl)-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid, 14-[5-((R)-{[(3R,4S,5R)-5-(Aminomethyl)-4-hydroxy-3-methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-2,4-dioxo-3-pentyl-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid, 14-[5-((R)-{[(3R,4S,5R)-5-(Aminomethyl)-4-hydroxy-3-methoxytetrahydro-2-furanyl]oxy}{((2S,3S,4R,5R)-5-[2,4-dioxo-3,4-dihydro-1 (2H)-pyrimidinyl]-3,4-dihydroxytetrahydro-2-furanyl}methyl)-3-hexyl-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid, 14-[5-((R)-{[(3R,4S,5R)-5-(Aminomethyl)-4-hydroxy-3-methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-3-(4-methoxyphenyl)-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid, 14-[5-((R)-{[(3R,4S,5R)-5-(Aminomethyl)-4-hydroxy-3-methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-3-dodecyl-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid, 16-((R)-{[(3R,4S,5R)-5-(Aminomethyl)-4-hydroxy-3-methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-15-benzyl-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid, 16-((R)-{[(3R,4S,5R)-5-(Aminomethyl)-4-hydroxy-3-methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-15-dodecyl-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid, 16-((R)-{[(3R,4S,5R)-5-(Aminomethyl)-4-hydroxy-3-methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-15-[12-(4-morpholinyl)dodecyl]-4,7,10-trioxo-3,5,8,11,15-pentaazaheptadecane-1,17-dioic acid, 16-((R)-{[(3R,4S,5R)-5-(Aminomethyl)-4-hydroxy-3-methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-15-pentyl-3,5,8,11,15-pentaazaheptadecane-1,17-dioic acid, 4-[13-((2R)-2-{[(3R,4S,5R)-5-(Aminomethyl)-4-hydroxy-3-methoxytetrahydro-2-furanyl]oxy}-1-carboxy-2-{(2S,3S,4R,5R)-5-[2,4-dioxo-3,4-dihydro-1 (2H)-pyrimidinyl]-3,4-dihydroxytetrahydro-2-furanyl}ethyl)-26-carboxy-19-(1-hydroxy-2-methylpropyl)-22-(2-iminohexahydro-4-pyrimidinyl)-27-methyl-18,21,24-trioxo-13,17,20,23,25-pentaazaoctacos-1-yl]-4-methylmorpholin-4-ium, 14-[5-((R)-{(2S,3S,4R,5R)-5-[2,4-Dioxo-3,4-dihydro-1 (2H)-pyrimidinyl]-3,4-dihydroxytetrahydro-2-furanyl}{[(3R,4S,5R)-4-hydroxy-3-methoxy-5-({[(octylamino)carbonyl]amino}methyl)tetrahydro-2-furanyl]oxy}methyl)-3-octyl-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid, 14-[5-((R)-{(2S,5R)-5-[2,4-Dioxo-3,4-dihydro-1 (2H)-pyrimidinyl]-3,4-dihydroxytetrahydro-2-furanyl}{[(5R)-4-hydroxy-3-methoxy-5-({[(4-fluoroanilino)carbonyl]amino}methyl)tetrahydro-2-furanyl]oxy}methyl)-3-(4-fluorophenyl)-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid, 14-[5-((R)-{(2S,5R)-5-[2,4-Dioxo-3,4-dihydro-1 (2H)-pyrimidinyl]-3,4-dihydroxytetrahydro-2-furanyl}{[(5R)-4-hydroxy-3-methoxy-5-({[(4-methoxyanilino)carbonyl]amino}methyl)tetrahydro-2-furanyl]oxy}methyl)-3-(4-methoxyphenyl)-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid, 14-[5-((R)-{(2S,3S,4R,5R)-5-[2,4-Dioxo-3,4-dihydro-1 (2H)-pyrimidinyl]-3,4-dihydroxytetrahydro-2-furanyl}{[(3R,4S,5R)-5-({[(hexylamino)carbonyl]amino}methyl)-4-hydroxy-3-methoxytetrahydro-2-furanyl]oxy}methyl)-3-hexyl-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid, 14-[5-((R)-{(2S,3S,4R,5R)-5-[2,4-Dioxo-3,4-dihydro-1 (2H)-pyrimidinyl]-3,4-dihydroxytetrahydro-2-furanyl}{[(3R,4S,5R)-5-({[(dodecylamino)carbonyl]amino}methyl)-4-hydroxy-3-methoxytetrahydro-2-furanyl]oxy}methyl)-3-dodecyl-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid, 16-((R)-{(2S,3S,4R,5R)-5-[2,4-Dioxo-3,4-dihydro-1 (2H)-pyrimidinyl]-3,4-dihydroxytetrahydro-2-furanyl}{[(3R,4S,5R)-5-({[(hexadecylamino)carbonyl]amino}methyl)-4-hydroxy-3-methoxytetrahydro-2-furanyl]oxy}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid, 16-[(R)-{(2S,3S,4R,5R)-5-[2,4-Dioxo-3,4-dihydro-1 (2H)-pyrimidinyl]-3,4-dihydroxytetrahydro-2-furanyl}({(3R,4S,5R)-4-hydroxy-3-methoxy-5-[(pentylamino)methyl]tetrahydro-2-furanyl}oxy)methyl]-9-(1-hydroxy-2-methylpropyl)-6-(2-iminohexahydro-4-pyrimidinyl)-2-isopropyl-4,7,10-trioxo-15-pentyl-3,5,8,11,15-pentaazaheptadecane-1,17-dioic acid, 16-[(R)-{(2S,3S,4R,5R)-5-[2,4-Dioxo-3,4-dihydro-1 (2H)-pyrimidinyl]-3,4-dihydroxytetrahydro-2-furanyl}({(3R,4S,5R)-4-hydroxy-3-methoxy-5-[(pentylamino)methyl]tetrahydro-2-furanyl}oxy)methyl]-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid, 16-((R)-[((3R,4S,5R)-5-{[([1,1'-Biphenyl]-4-ylmethyl)amino]methyl}-4-hydroxy-3-methoxytetrahydro-2-furanyl)oxy]{(2S,3S,4R,5R)-5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid, 15-([1,1'-Biphenyl]-4-ylmethyl)-16-((R)-[((3R,4S,5R)-5-{[([1,1'-biphenyl]-4-ylmethyl)amino]methyl}-4-hydroxy-3-methoxytetrahydro-2-furanyl)oxy]{(2S,3S,4R,5R)-5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid, 16-((R)-({(3R,4S,5R)-5-[(Benzylamino)methyl]-4-hydroxy-3-methoxytetrahydro-2-furanyl}oxy){(2S,3S,4R,5R)-5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid, 15-Benzyl-16-((R)-({(3R,4S,5R)-5-[(benzylamino)methyl]-4-hydroxy-3-methoxytetrahydro-2-furanyl}oxy){(2S,3S,4R,5R)-5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid, and 16-((R)-({(3R,4S,5R)-5-[(Acetamido)methyl]-4-hydroxy-3-methoxytetrahydro-2-furanyl}oxy){(2S,3S,4R,5R)-5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid.

For the compounds of the invention defined above and referred to herein, unless otherwise noted, the following terms are defined:

Halogen, as used herein means fluoro, chloro, bromo and/or iodo.

Alkyl as used herein means a branched or straight chain radical having from 1 to 20 (preferably 1 to 16) or preferably (1 to 12)carbon atoms optionally substituted with morpholino where the morpholino nitrogen atom may optionally be alkylated with alkyl of 1 to 6 carbon atoms forming a quaternary salt. Exemplary alkyl groups include but are not limited to methyl, ethyl, propyl, isopropyl, butyl, isobutyl, t-butyl, pentyl and hexyl, also optionally substituted, as well as perfluoroalkyl.

Aryl as used herein means a homocyclic or polycyclic aromatic radical, having 6 to 20 carbon atoms independently substituted with one to three substituents selected from the group of alkyl, halogen, cyano, nitro, hydroxy, , amino, alkylamino, dialkylamino, or alkoxy. Examples include, but are not limited to, phenyl, biphenyl, naphthyl, fluorenyl, and anthracenyl, optionally substituted with one to three substituents.

The preparation of 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid by fermentation is described in copending application Ser. No. 60/286,402 filed Apr. 25, 2001 incorporated herein by reference and copending application Ser. No. 60/290,156 filed May 10, 2001 incorporated herein by reference.

DETAILED DESCRIPTION OF INVENTION

Figure 1:
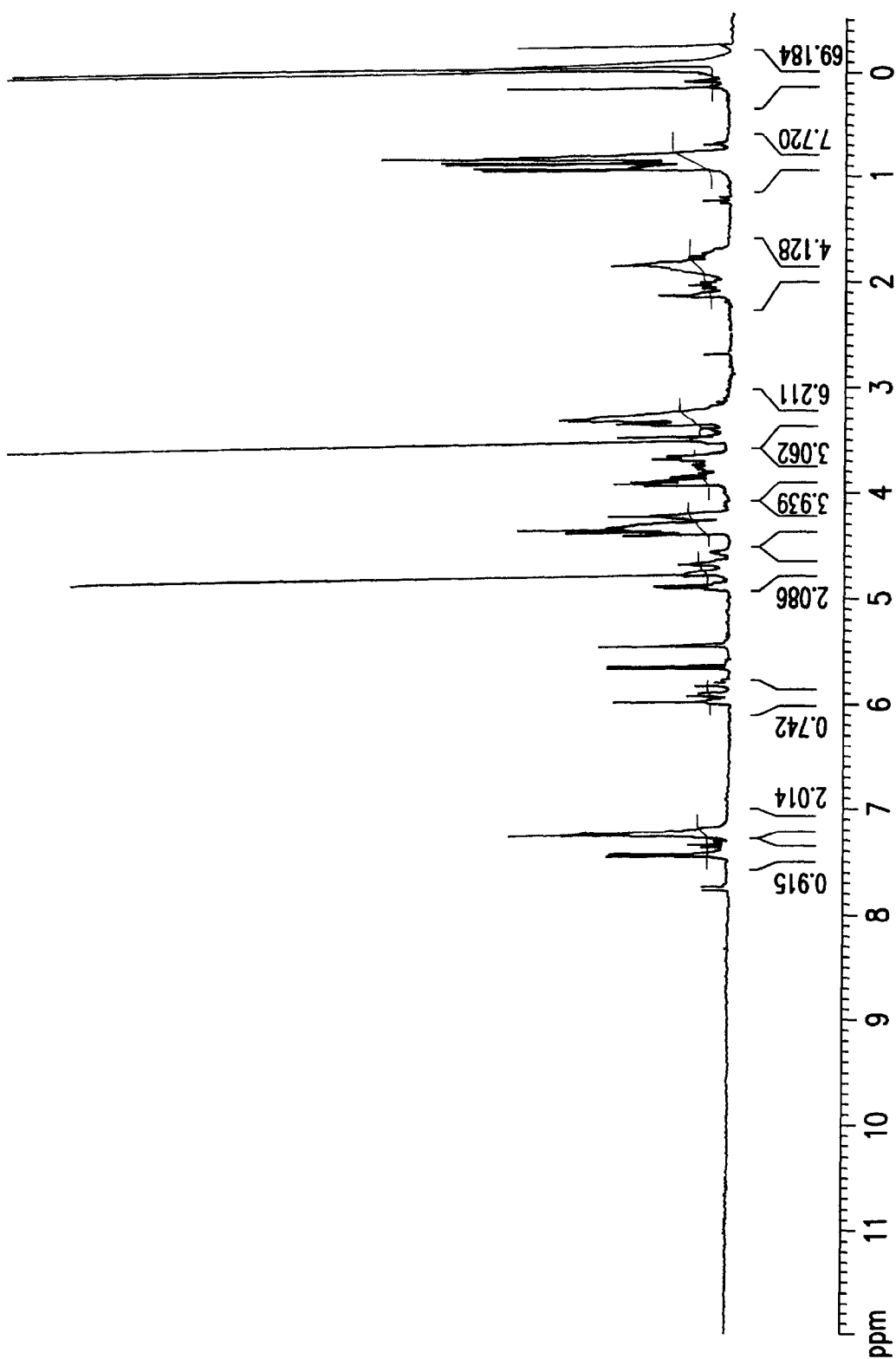
FIG. 1. Proton NMR spectrum of Example 1 in $D_2O$ at 300 MHz

The compounds of the invention are prepared according to the following reaction schemes.

As shown in Scheme 1, protecting the primary amine of 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid 1 with 2,4-pentanedione in pyridine and methanol is followed by reaction with an isocyanate $R_4NCO$ 2 in a solvent such as N,N-dimethylformamide with later removal of the amine protecting group using 0.5% trifluoroacetic acid in water and dioxane to give carboxylic acid 3.

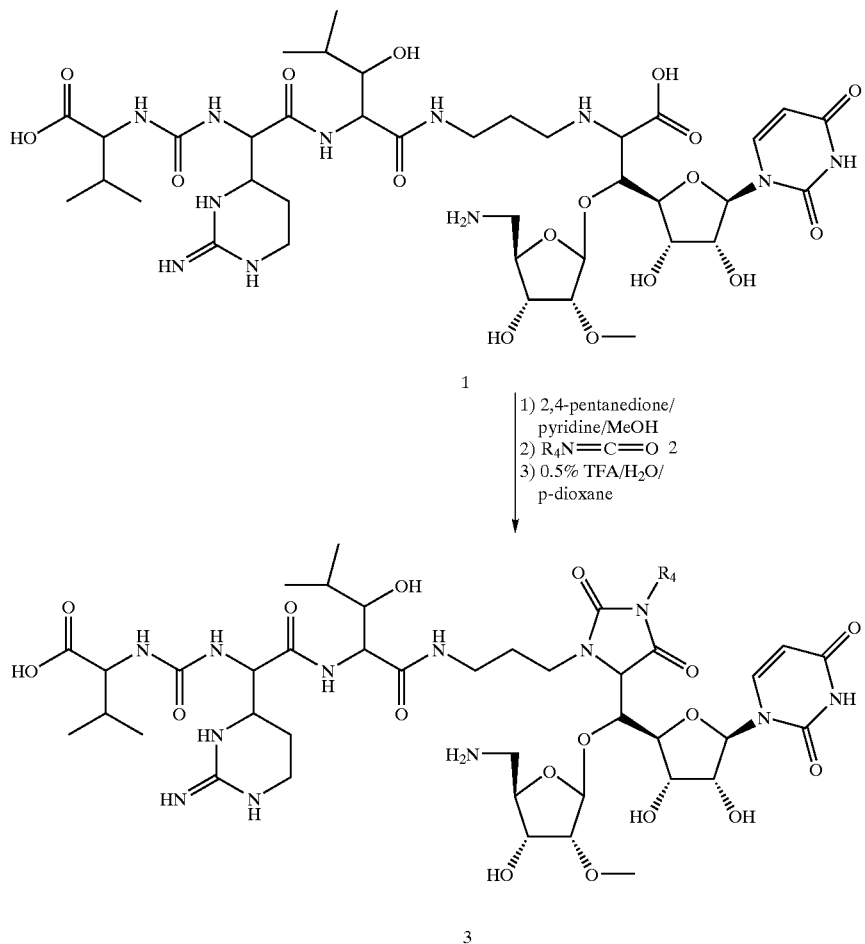

SCHEME 1

In accordance with Scheme 2, 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid 1 is reacted with 2,4-pentanedione, to protect the primary amine, followed by reaction with arylCH$_2$Br 4 in a solvent such as N,N-dimethylformamide followed by removal of the protecting group with 0.5% trifluoroacetic acid in water and dioxane affords dicarboxylic acid 5.

SCHEME 2

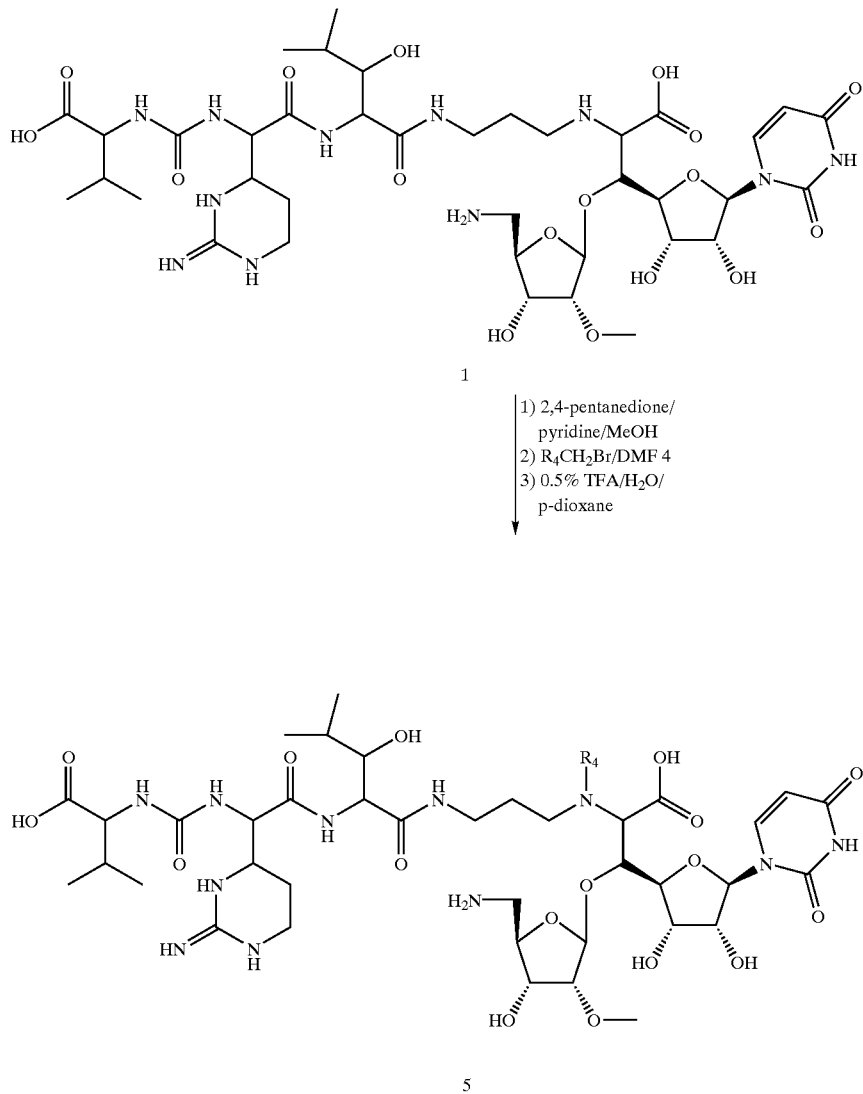

As shown in Scheme 3, reaction of 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid 1 having the primary amine protected with 2,4-pentanedione followed by reductive alkylation by reaction with $R_4CHO$ 6 in a solvent such as N,N-dimethylformamide followed by treatment with either sodium cyanoborohydride or sodium triacetoxyborohydride and then removal of the primary amine protecting group with 0.5% trifluoroacetic acid in water and dioxane affords alkylated derivatives 7.

SCHEME 3

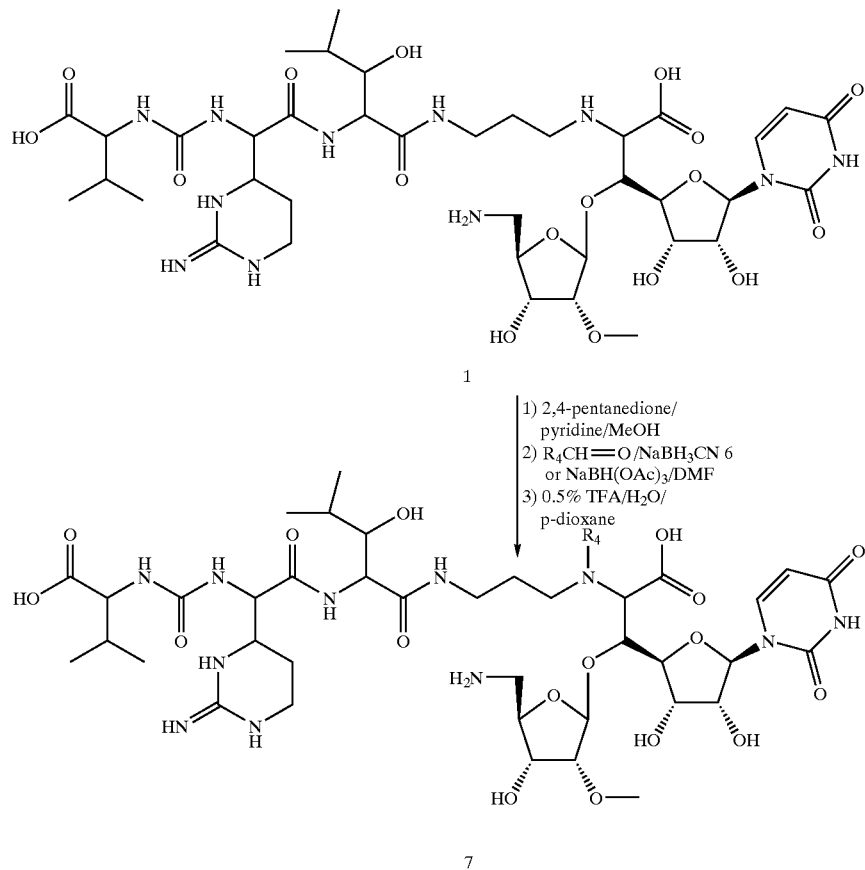

As shown in Scheme 4, reaction of 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid 1 with $R_4NCO$ 2 in a solvent such as N,N-dimethylformamide followed by treatment with water affords dialkylated derivatives 8.

SCHEME 4

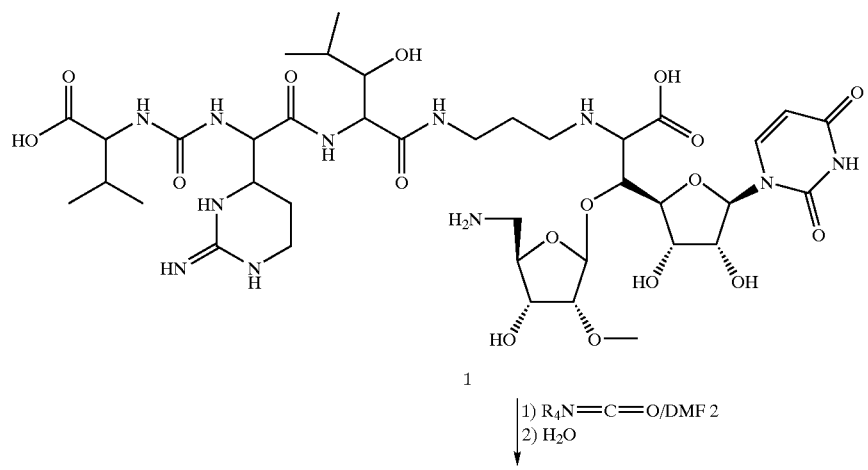

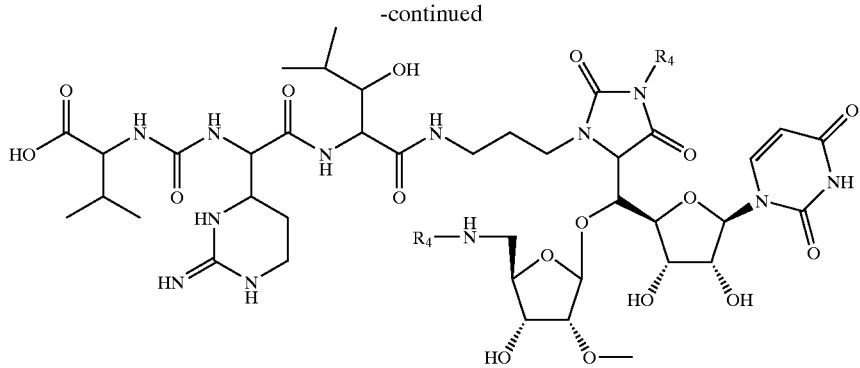

8

In accordance with Scheme 5, reaction of 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid 1, by reductive alkylation with $R_4CHO$ 6 in a solvent such as N,N-dimethylformamide followed by treatment with either sodium cyanoborohydride or sodium triacetoxyborohydride affords dialkylated derivatives 9 or monoalkylated derivatives 9a.

SCHEME 5

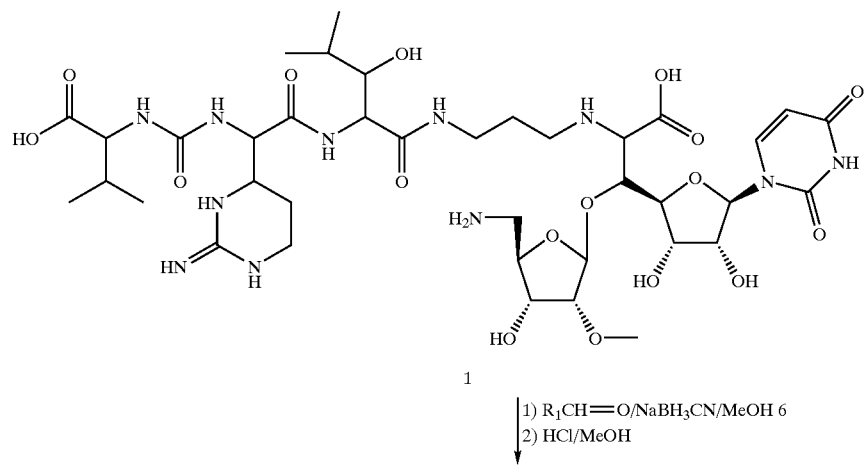

1) $R_1CH=O/NaBH_3CN/MeOH$ 6
2) HCl/MeOH

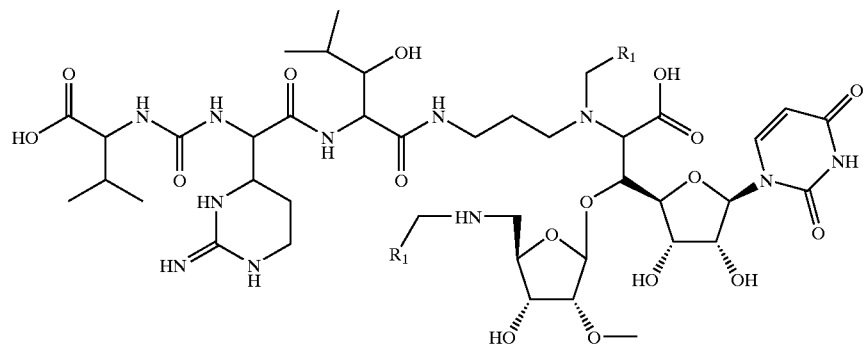

9

-continued

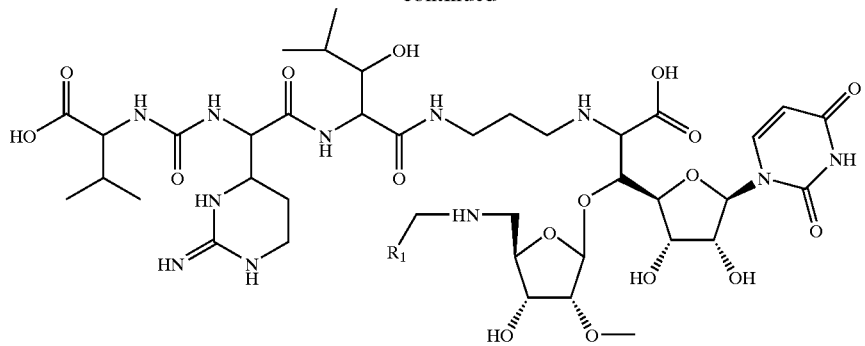

9a

As shown in Scheme 6, reaction of 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid 1, with acetic anhydride ($Ac_2O$) at room temperature affords derivative 10.

invention may be obtained as pharmaceutically acceptable salts which are those derived from such organic and inorganic acids as:

acetic, trifluoroacetic, lactic, citric, tartaric, formate, succinic, maleic, malonic, gluconic, hydrochloric, hydrobromic, phosphoric, nitric, sulfuric, methanesulfonic, and similarly known acceptable acids. Additionally, compounds of the invention may form calcium, potassium, magnesium, or sodium salts. The

SCHEME 6

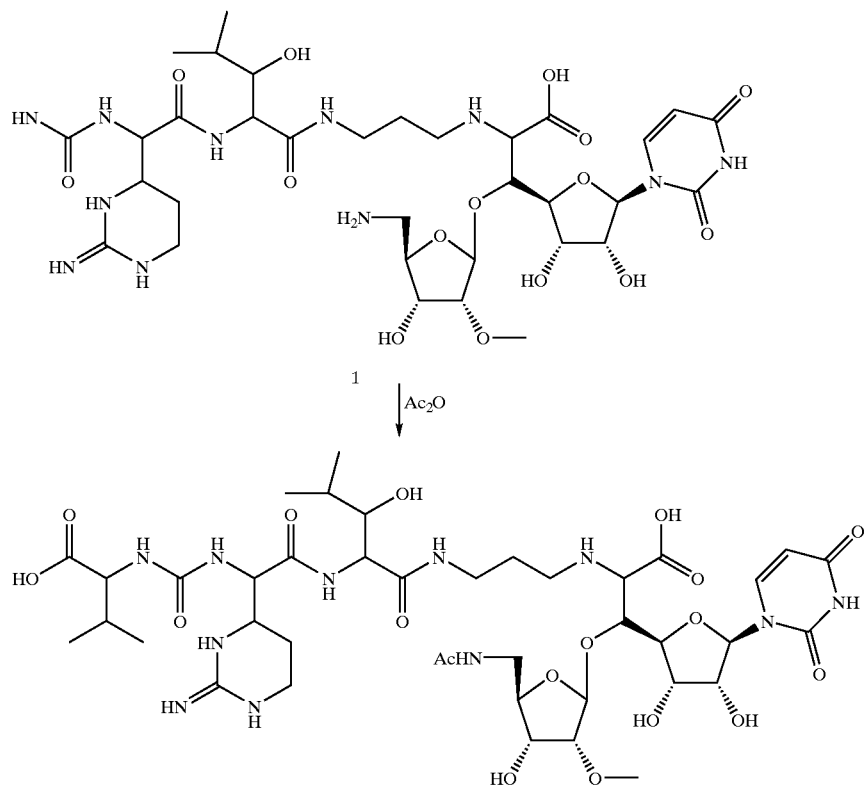

It is understood that compounds of this invention encompasses all crystalline forms. Further, compounds of the pharmaceutically acceptable salts of compounds of the invention are prepared using conventional procedures.

Compounds of the invention have centers of asymmetry. The compounds of the invention may, therefore, exist in at least two and often more stereoisomeric forms. The present invention encompasses all stereoisomers whether free from other stereoisomers or admixed with other stereoisomers in any proportion and thus includes, for instance, racemic mixtures of enantiomers as well as the diastereomeric mixtures of isomers. The absolute configuration of any substantially pure compound may be determined by any suitable method including conventional X-ray crystallography.

The present invention accordingly provides a pharmaceutical composition which comprises a compound of the invention or a mixture thereof in combination or association with a pharmaceutically acceptable carrier. In particular, the present invention provides a pharmaceutical composition which comprises an effective amount of compounds of the invention or a mixture thereof and a pharmaceutically acceptable carrier.

The present invention also provides methods which may be used in treating bacterial infections in warm blooded animals which comprise providing to said animals an antibacterially effective amount of a compound of the invention or a mixture thereof.

Biological Activity

In Vitro Evaluation of AA-896 Derivatives as Antibacterial Agents

The in vitro antibacterial activity of Example 1 through Example 20 is determined against a spectrum of Gram-positive and Gram-negative bacteria by a standard broth dilution method. Serial dilution of the compounds are made in Mueller-Hinton broth and inoculated with a bacterial suspension. The lowest concentration of compound that inhibited the growth of a bacterial strain after 18 hours of incubation at 35° C. is reported as the minimal inhibitory concentration (MIC) for that strain. The results are given in Table 1.

TABLE 1

Antimicrobial Activity (MIC, $\mu$g/mL) of AA-896 Derivatives

| | Example 1 | Example 2 | Example 3 | Example 4 | Example 5 | Example 6 |
|---|---|---|---|---|---|---|
| E. coli GC 4559 | >32 | >32 | >32 | >32 | >32 | >32 |
| E. coli GC 4560 | 64 | 32 | 32 | >32 | 4 | 2 |
| E. coli GC 3226 | >32 | >32 | >32 | >32 | >32 | >32 |
| S. marcescens GC 4077 | >32 | >32 | >32 | >32 | >32 | >32 |
| P. rettgeri GC 4530 | >32 | >32 | >32 | >32 | >32 | >32 |
| M. morganii GC 4531 | >32 | >32 | >32 | >32 | >32 | >32 |
| K. pneumoniae GC 4534 | >32 | >32 | >32 | >32 | >32 | >32 |
| E. cloacae GC 3783 | >32 | >32 | >32 | >32 | >32 | >32 |
| P. aeruginosa GC 4532 | >32 | >32 | >32 | >32 | >32 | >32 |
| S. aureus GC 4536 | >32 | >32 | >32 | >32 | >32 | >32 |
| S. aureus GC 1131 | >32 | >32 | >32 | >32 | >32 | >32 |
| CNS GC 4537 | >32 | >32 | >32 | >32 | >32 | >32 |
| CNS GC 4538 | 32 | >32 | >32 | >32 | >32 | >32 |
| CNS GC 4547 | >32 | >32 | >32 | >32 | >32 | >32 |
| E. faecalis GC 842 | >32 | >32 | >32 | >32 | >32 | >32 |
| E. faecalis GC 2242 | >32 | >32 | >32 | >32 | >32 | >32 |
| E. coli GC 2203 | >32 | >32 | >32 | >32 | >32 | >32 |
| P. aeruginosa GC 2214 | >32 | >32 | >32 | >32 | >32 | >32 |
| S. aureus GC 2216 | >32 | >32 | >32 | >32 | >32 | >32 |
| E. faecalis GC 4555 | >32 | >32 | >32 | >32 | >32 | >32 |

| | Example 7 | Example 8 | Example 9 | Example 10 | Example 11 | Example 12 | Example 13 |
|---|---|---|---|---|---|---|---|
| E. coil GC 4559 | >32 | >32 | >32 | >32 | >32 | >32 | >32 |
| E. coli GC 4560 | 16 | >32 | 32 | 16 | >32 | >32 | >32 |
| E. coli GC 3226 | >32 | >32 | >32 | >32 | >32 | >32 | >32 |
| S. marcescens GC 4077 | >32 | >32 | >32 | >32 | >32 | >32 | >32 |
| P. rettgeri GC 4530 | >32 | >32 | >32 | >32 | >32 | >32 | >32 |
| M. morganii GC 4531 | >32 | >32 | >32 | >32 | >32 | >32 | >32 |
| K. pneumoniae GC 4534 | >32 | >32 | >32 | >32 | >32 | >32 | >32 |
| E. cloacae GC 3783 | >32 | >32 | >32 | >32 | >32 | >32 | >32 |
| P. aeruginosa GC 4532 | >32 | >32 | >32 | >32 | >32 | >32 | >32 |
| S. aureus GC 4536 | >32 | >32 | >32 | >32 | >32 | >32 | >32 |
| S. aureus GC 1131 | >32 | >32 | >32 | >32 | >32 | >32 | >32 |
| CNS GC 4537 | >32 | >32 | >32 | >32 | >32 | >32 | >32 |

TABLE 1-continued

Antimicrobial Activity (MIC, μg/mL) of AA-896 Derivatives

| | | | | | | | |
|---|---|---|---|---|---|---|---|
| CNS GC 4538 | >32 | >32 | >32 | >32 | >32 | >32 | >32 |
| CNS GC 4547 | >32 | >32 | >32 | >32 | >32 | >32 | >32 |
| E. faecalis GC 842 | >32 | >32 | >32 | >32 | >32 | >32 | >32 |
| E. faecalis GC 2242 | >32 | >32 | >32 | >32 | >32 | >32 | >32 |
| E. coli GC 2203 | >32 | >32 | >32 | >32 | >32 | >32 | >32 |
| P. aeruginosa GC 2214 | >32 | >32 | >32 | >32 | >32 | >32 | >32 |
| S. aureus GC 2216 | >32 | >32 | >32 | >32 | >32 | >32 | >32 |
| E. faecalis GC 4555 | >32 | >32 | >32 | >32 | >32 | >32 | >32 |

| | Example 14 | Example 15 | Example 16 | Example 17 | Example 18 |
|---|---|---|---|---|---|
| E. coli GC 4559 | >32 | >32 | >32 | >32 | >32 |
| E. coli GC 4560 | 32 | >32 | >32 | 32 | >32 |
| E. coli GC 3226 | >32 | >32 | >32 | >32 | >32 |
| S. marcescens GC 4077 | >32 | >32 | >32 | >32 | >32 |
| P. rettgeri GC 4530 | >32 | >32 | >32 | >32 | >32 |
| M. morganii GC 4531 | >32 | >32 | >32 | >32 | >32 |
| K. pneumoniae GC 4534 | >32 | >32 | >32 | >32 | >32 |
| E. cloacae GC 3783 | >32 | >32 | >32 | >32 | >32 |
| P. aeruginosa GC 4532 | >32 | >32 | >32 | >32 | >32 |
| S. aureus GC 4536 | 32 | >32 | >32 | >32 | >32 |
| S. aureus GC 1131 | 32 | >32 | >32 | >32 | >32 |
| CNS GC 4537 | 32 | >32 | >32 | >32 | >32 |
| CNS GC 4538 | 32 | >32 | >32 | >32 | >32 |
| CNS GC 4547 | 16 | >32 | >32 | 32 | >32 |
| E. faecalis GC 842 | >32 | >32 | >32 | >32 | >32 |
| E. faecalis GC 2242 | 32 | >32 | >32 | 32 | >32 |
| E. coli GC 2203 | >32 | >32 | >32 | >32 | >32 |
| P. aeruginosa GC 2214 | >32 | >32 | >32 | >32 | >32 |
| S. aureus GC 2216 | 32 | >32 | >32 | >32 | >32 |
| E. faecalis GC 4555 | >32 | >32 | >32 | >32 | >32 |

| | Example 19A | Example 19B | Example 20A | Example 20B |
|---|---|---|---|---|
| E. coli GC 4559 | >32 | >32 | >32 | >32 |
| E. coli GC 4560 | 16 | >32 | >32 | 32 |
| E. coli GC 3226 | >32 | >32 | >32 | >32 |
| S. marcescens GC 4077 | >32 | >32 | >32 | >32 |
| P. rettgeri GC 4530 | >32 | >32 | >32 | >32 |
| M. morganii GC 4531 | >32 | >32 | >32 | >32 |
| K. pneumoniae GC 4534 | >32 | >32 | >32 | >32 |
| E. cloacae GC 3783 | >32 | >32 | >32 | >32 |
| P. aeruginosa GC 4532 | >32 | >32 | >32 | >32 |
| S. aureus GC 4536 | >32 | >32 | >32 | >32 |
| S. aureus GC 1131 | >32 | >32 | >32 | >32 |
| CNS GC 4537 | >32 | >32 | >32 | >32 |
| CNS GC 4538 | >32 | >32 | >32 | >32 |
| CNS GC 4547 | >32 | >32 | >32 | >32 |
| E. faecalis GC 842 | >32 | >32 | >32 | >32 |
| E. faecalis GC 2242 | >32 | >32 | >32 | >32 |
| E. coli GC 2203 | >32 | >32 | >32 | >32 |
| P. aeruginosa GC 2214 | >32 | >32 | >32 | >32 |
| S. aureus GC 2216 | >32 | >32 | >32 | >32 |
| E. faecalis GC 4555 | >32 | >32 | >32 | >32 |

Determination of Lipid II Formation by a TLC Methodology

The MurG biochemical assay utilizes *S. epidermides* membranes to catalyze the late steps in cell wall biosynthesis including MraY, the phospho-MurNAc pentapeptide translocase and MurG, the UDP-N-Acetylglucosaminyl transferase. The following procedure is adapted from the method described by Mengin-Lecreaulx, et al (*J. Bacteriol* 173(15) 4625–4636, 1991). In this procedure, the formation of Lipid II is assessed using radiolabeled UDP-N-Acetylglucosamine.

*S. epidermides* membranes, compound, UDP-MurNAc pentapeptide, and [$^{14}$C]-UDP-N-Acetylglucosamine were incubated at room temperature for 30 min. The reaction was terminated by boiling in a water bath for 1 minute. 2 μl samples of each reaction are analyzed by TLC. The samples are spotted onto K6 silica plates and chromatographed in Isobutyric Acid:1 M NH$_4$OH (5:3). The plates are exposed to film and the inhibition of Lipid II formation can be monitored by comparing the sample area to the control area.

| $IC_{50}$ | 100 µg/ml | 50 µg/ml | 25 µg/ml | 6.25 µg/ml |
|---|---|---|---|---|
| Example 1 | + | + | + | − |
| Example 2 | + | − | − | − |
| Example 5 | + | + | + | + |
| Example 6 | + | + | + | + |
| Example 7 | + | + | − | − |
| Example 8 | + | − | − | − |
| Example 9 | + | − | − | − |
| Example 11 | − | − | − | − |
| Example 12 | − | − | − | − |
| Example 13 | − | − | − | − |
| Example 14 | − | − | − | − |
| Example 15 | − | − | − | − |
| Example 16 | + | − | − | − |
| Example 17 | − | − | − | − |
| Example 19A | + | + | + | − |
| Example 19B | − | − | − | − |

Compounds of the invention derive their utility from their antibacterial activity. For example, these compounds may be used in the suppression of bacterial infections, as a topical antibacterial agent and as a general disinfectant for laboratories.

In therapeutic use, the compounds of this invention may be administered in the form of conventional pharmaceutical compositions appropriate for the intended use. Such compositions may be formulated so as to be suitable for oral, parenteral or topical administration. The compounds of the invention may be combined in admixture with a nontoxic pharmaceutical carrier, which carrier may take a variety of forms, depending on the form of preparation desired for administration, ie. oral, parenteral, or topical.

When the compounds of the invention are employed for the above utility, they can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example from about 10 to 50% of sugar, and elixirs containing, for example from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 0.05 up to about 90% of the compounds of the invention in combination with the carrier, more usually between about 5% and 60% by weight.

An antibacterially effective amount of compounds of the invention from about 0.5 mg/kg of body weight to about 200.0 mg/kg of body weight should be administered one to five times per day via any topical routes of administration including but not limited to oral, parenteral (including subcutaneous, intravenous, intramuscular, intrasternal injection or infusion techniques), by inhalation spray, or rectally, in dosage unit formulations containing conventional nontoxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sec, diet, mode and time of administration, rate of excretion, drug combination, the severity of the particular condition, and the host undergoing therapy.

Additionally, the antibacterially effective amount of the compounds of the invention may be administered at a dosage and frequency without inducing side effects commonly experienced with conventional antibiotic therapy which could include hypersensitivity, neuromuscular blockade, vertigo, photosensitivity, discoloration of teeth, hematologic changes, gastrointestinal disturbances, ototoxicity, and renal, hepatic, or cardiac impairment. Further the frequency and duration of dosage may be monitored to substantially limit harmful effects to normal tissues caused by administration at or above the antibacterially effective amount of the substantially pure compounds of the invention.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA. The preferred pharmaceutical compositions from the stand-point of ease of preparation and administration are solid compositions, particularly tablets and hard-filled or liquid-filled capsules. Oral administration of the compound is preferred. The compounds of the invention may also be administered parenterally or intraperitoneally. Solutions or suspensions of these active compounds as a free base or pharmacologically acceptable salt can be prepared in water suitably mixed with a surfactant such as hydroxy propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oil. The invention will be further described in conjunction with the following non-limiting examples.

EXAMPLE 1

14-[5-((R)-{[(3R,4S,5R)-5-(Aminomethyl)-4-hydroxy-3-methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-3-(4-fluorophenyl)-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid To a solution of 47.3 mg (50 μmol) of 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11, 15-pentaazaheptadecane-1,17-dioic acid $\lambda_{max}$ nm in water=259) in 2.5 ml of methanol is added 200 μl of pyridine and 200 μl of 2,4-pentanedione at room temperature. The reaction mixture is stirred overnight (the reaction is monitored by mass spectroscopy (MS)). After the reaction is complete, the volatile materials are removed under reduced pressure. N,N-dimethylformamide (DMF) (3 ml) is added to the residue, followed by addition of 13.0 mg (95 μmol) of 4-fluorophenyl isocyanate. The reaction mixture is stirred at room temperature for 50 hours (the reaction was monitored by MS). The volatile materials are removed under reduced pressure to afford a residue to which is added 5 ml of 0.5% trifluoroacetic acid (TFA) in a 1:1 mixture of water and p-dioxane. The mixture is stirred at room temperature for 2 hours. The reaction is monitored by MS and the desired product is identified by liquid chromatography/mass spectrum (LC/MS). After concentration of volatiles to about one ml, 24 mg (44% yield) of the desired product is obtained as a colorless solid using preparative high pressure liquid chromatography (HPLC).

HPLC conditions:

column: Prodigy ODS 4.6×150 mm mobile phase: gradient, A=0.02% TFA/water; B=0.02% TFA/acetonitrile flow rate: 1.0 ml/min detection: 215 nm, MSD retention time: 5.1 min Molecular formula: $C_{45}H_{65}FN_{12}O_{17}$;

Molecular weight: positive ion electrospray MS m/z= 1065.2 (M+H)$^+$ and 533.2 (M+2H)$^2$;

Proton magnetic resonance spectrum (300 Mhz D$_2$O): FIG. 1;

Ultraviolet absorption spectrum: $\lambda_{max}$ nm (water)=261.

EXAMPLE 2

14-[5-((R)-{[(3R,4S,5R)-5-(Aminomethyl)-4-hydroxy-3-methoxytetrahydro-2furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-2,4-dioxo-3-pentyl-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid The title compound is prepared by the procedure of Example 1, using 24.0 mg (25 μmol) of 16-({[5-(aminomethyl)-4-hydroxy-3-methoxytetrahydro-2-furanyl]oxy}{5-[2,4-dioxo-3,4-dihydro-1(2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid $\lambda_{max}$ nm in water=259) in 1.0 ml of methanol, 100 μl of pyridine, 100 μl of 2,4-pentanedione and 30 μmol of pentylisocyanate to give 17 mg of the desired product.

Molecular formula: $C_{44}H_{72}N_{12}O_{17}$;

Molecular weight: positive ion electrospray MS m/z= 1041.5 (M+H)$^+$ and 521.4 (M+2H)$^{2+}$.

EXAMPLE 3

14-[5-((R)-{[(3R,4S,5R)-5-(Aminomethyl)-4-hydroxy-3-methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-3-hexyl-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid The title compound is prepared by the procedure of Example 1, using 47.3 mg (50 μmol) of 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid ($\lambda_{max}$ nm in water=259) in 3.0 ml of methanol, 200 μl of pyridine, 200 μl of 2,4-pentanedione and 50 μmol of hexylisocyanate to give 15 mg of the desired product.

HPLC conditions:

column: Prodigy ODS 4.6×150 mm mobile phase: gradient, A=0.02% TFA/water; B=0.02% TFA/acetonitrile flow rate: 1.0 ml/min detection: 215 nm, MSD retention time: 5.3 min Molecular formula: $C_{45}H_{74}N_{12}O_{17}$;

Molecular weight: positive ion electrospray MS m/z= 528.4 (M+2H)$^{2+}$.

EXAMPLE 4

14-[5-((R)-{[(3R,4S,5R)-5-(Aminomethyl)-4-hydroxy-3-methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-3-(4-methoxyphenyl)-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid The title compound is prepared by the procedure of Example 1, using 47.3 mg (50 μmol) of 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid ($\lambda_{max}$ nm in water=259) in 3.0 ml of methanol, 200 μl of pyridine, 200 μl of 2,4-pentanedione and 55 μmol of 4-methoxyphenylisocyanate to give 16 mg of the desired product.

HPLC conditions:

column: Prodigy ODS 4.6×150 mm mobile phase: gradient, A=0.02% TFA/water; B=0.02% TFA/acetonitrile flow rate: 1.0 ml/min detection: 215 nm, MSD retention time: 7.31 min Molecular formula: $C_{46}H_{68}N_{12}O_{18}$;

Molecular weight: positive ion electrospray MS m/z= 539.5 $(M+2H)^{2+}$.

EXAMPLE 5

14-[5-((R)-{[(3R,4S,5R)-5-(Aminomethyl)-4-hydroxy-3-methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-3-dodecyl-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid The title compound is prepared by the procedure of Example 1, using 56.8 mg (60 μmol) of 16-({[5-(aminomethyl)-4-hydroxy-3-methoxytetrahydro-2-furanyl]oxy}{(5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid ($\lambda_{max}$ nm in water=259) in 3.5 ml of methanol, 240 μl of pyridine, 240 μl of 2,4-pentanedione and 66 μmol of dodecylisocyanate to give 15 mg of the desired product.

Figure 2:
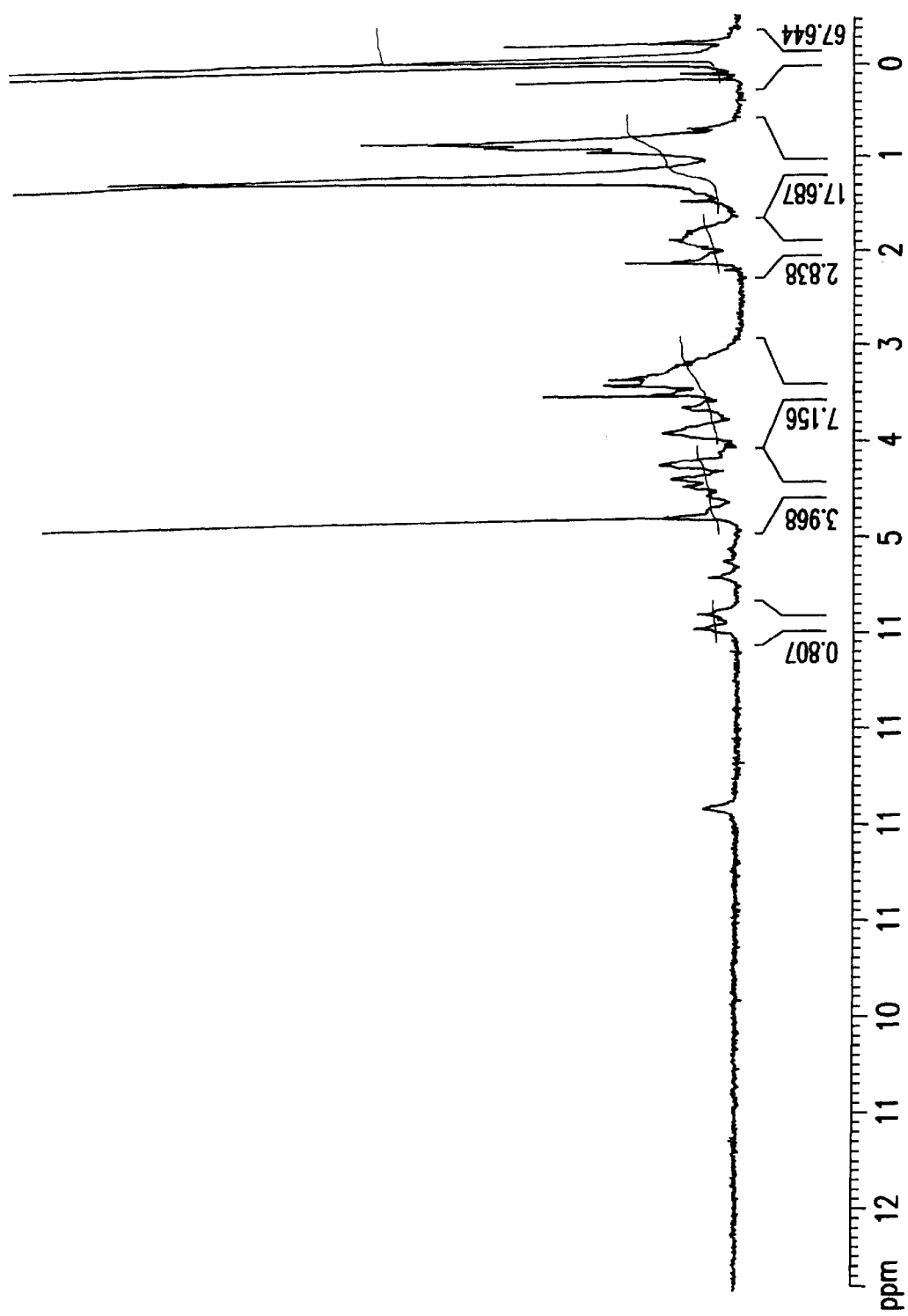
FIG. 2. Proton NMR spectrum of Example 5 in $D_2O$ at 300 MHz

HPLC conditions:

column: Prodigy ODS 4.6×150 mm mobile phase: gradient, A=0.02% TFA/water; B=0.02% TFA/acetonitrile flow rate: 1.0 ml/min detection: 215 nm, MSD retention time: 10.3 min Molecular formula: $C_{51}H_{86}N_{12}O_{17}$;

Molecular weight: positive ion electrospray MS m/z= 1139.4 $(M+H)^+$ and 570.3 $(M+2H)^{2+}$;

Proton magnetic resonance spectrum (300 Mhz $D_2O$): FIG. 2;

Ultraviolet absorption spectrum: $\lambda_{max}$ nm (water)=259.

EXAMPLE 6

16-((R)-{[(3R,4S,5R)-5-(Aminomethyl)-4-hydroxy-3-methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-15-benzyl-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic Acid To a solution of 56.8 mg (60 μmol) 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid ($\lambda_{max}$ nm in water=259) in 3.5 ml of methanol is added 240 μl of pyridine and 240 μl of 2,4-pentanedione at room temperature. The reaction mixture is stirred for 48 hours (the reaction is monitored by MS). After the reaction is complete, the volatile materials are removed under reduced pressure. N,N-Diemthylformamide (4 ml) is added to the residue, followed by addition of 12.3 mg (72 μmol) of benzyl bromide. The reaction mixture is stirred at room temperature overnight (the reaction is monitored by MS). The volatile materials are removed under reduced pressure to a residue to which is added 5 ml of 0.5% TFA in a 1:1 mixture of water:p-dioxane and the mixture is stirred at room temperature for 2 hours. The reaction is monitored by MS and the desired product identified by LC/MS. After the concentration of the reaction mixture to about one ml, 7 mg of the desired product is separated by preparative HPLC.

Figure 3:
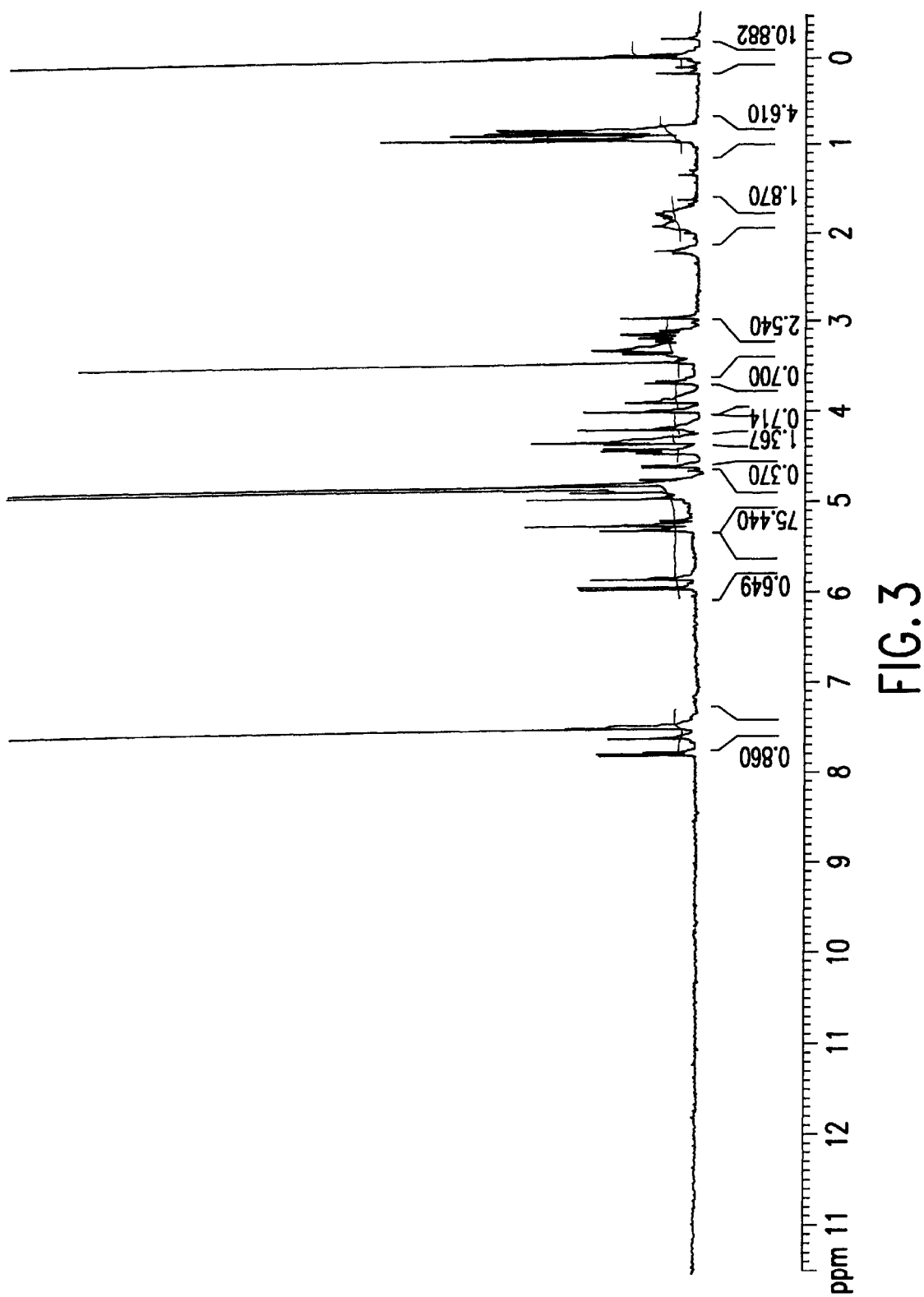
FIG. 3. Proton NMR spectrum of Example 6 in $D_2O$ at 300 MHz

HPLC conditions:

column: Prodigy ODS 4.6×150 mm mobile phase: gradient, A=0.02% TFA/water; B=0.02% TFA/acetonitrile flow rate: 1.0 m/min detection: 215 nm, MSD retention time: 5.8 min Molecular formula: $C_{45}H_{69}N_{11}O_{17}$;

Molecular weight: positive ion electrospray MS m/z= 1036.2 $(M+H)^+$ and 518.8 $(M+2H)^{2+}$;

Proton magnetic resonance spectrum (300 Mhz $D_2O$): FIG. 3.

EXAMPLE 7

16-((R)-{[(3R,4S,5R)-5-(Aminomethyl)-4-hydroxy-3-methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-15-dodecyl-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic Acid To a solution of 56.8 mg (60 μmol) of 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid ($\lambda_{max}$ nm in water=259) in 3.0 ml of methanol is added 300 μl of pyridine and 300 μl of 2,4-pentanedione at room temperature. The reaction mixture is stirred for 2 days (the reaction is monitored by MS). After the reaction is complete, the volatile materials are removed under reduced pressure. N,N-Dimethylformamide (3 ml) is added to the residue, followed by addition of 14.4 mg (78 μmol) of dodecyl aldehyde. The reaction mixture is kept at 70° C. for 0.5 hour, followed by addition of 78 μmol of sodium cyanoborohydride (NaBH₃CN), and the reaction mixture is heated at 70° C. (oil-bath) for an additional 2 hours (the reaction is also monitored by MS). The volatile materials are removed under reduced pressure to a residue to which is added 5 ml of 0.5% trifluoroacetic acid in a 1:1 mixture of water:p-dioxane and the reaction mixture stirred at room temperature for 2 hours. The reaction is monitored by MS and the desired product is identified by LC/MS. After concentration of the reaction mixture to about one ml, 21 mg of the desired product is separated by preparative HPLC.

Figure 4:
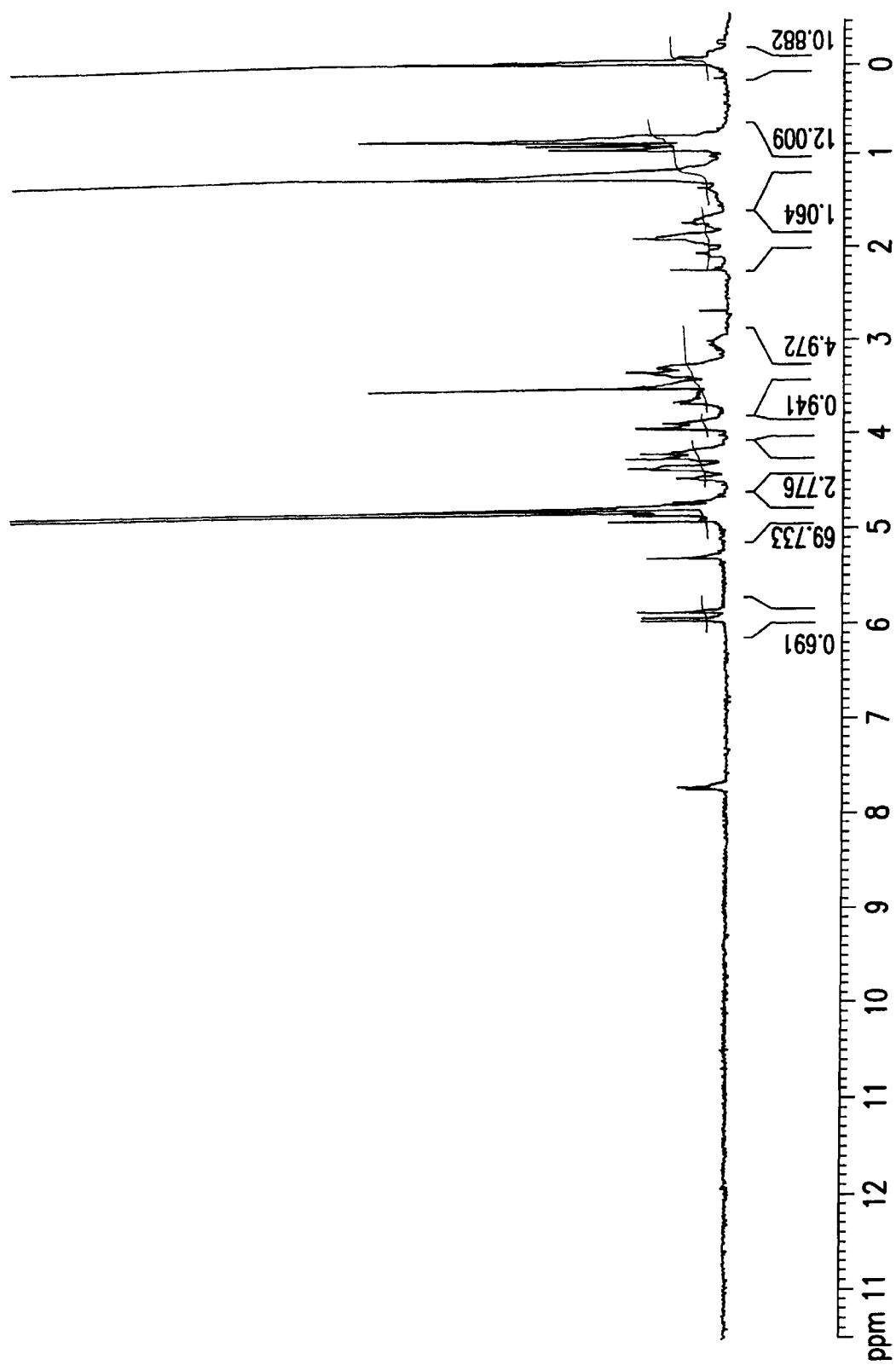
FIG. 4. Proton NMR spectrum of Example 7 in $D_2O$ at 300 MHz

HPLC conditions:
column: Prodigy ODS 4.6×150 mm
mobile phase: gradient, A=0.02% TFA/water; B=0.02% TFA/acetonitrile
flow rate: 1.0 ml/min
detection: 215 nm, MSD
retention time: 8.3 min
Molecular formula: $C_{50}H_{87}N_{11}O_{17}$;
Molecular weight: positive ion electrospray MS m/z= 1115.0 $(M+H)^+$ and 558.2 $(M+2H)^{2+}$;
Proton magnetic resonance spectrum (300 Mhz $D_2O$): FIG. 4;
Ultraviolet absorption spectrum: $\lambda_{max}$ nm (water)=260.

EXAMPLE 8

16-((R)-{[(3R,4S,5R)-5-(Aminomethyl)-4-hydroxy-3-methoxytetrahydro-2-furanyl]oxy}{(2S,3S,4R, 5R)-5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-15-[12-(4-morpholinyl) dodecyl]-4,7,10-trioxo-3,5,8,11,15-pentaazaheptadecane-1,17-dioic Acid To a solution of 66.2 mg (70 μmol) of 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid ($\lambda_{max}$ nm in water=259) in 3.0 ml of methanol is added 300 μl pyridine, 300 μl of 2,4-pentanedione and 30 mg montmorillonite K-10 (a clay forming the principal constituent of bentonite and fuller's earth(Merck Index, 11, 6168)) at room temperature. The reaction mixture is stirred for 2 days and monitored by MS. After the reaction is completion, the reaction mixture is filtered, and washed with methanol. The volatile materials are removed under reduced pressure to a residue to which is added N,N-Dimethylformamide (3 ml) followed by additon of 66 mg (245 μmol) of 12-(4-morpholinyl)dodecanal (see examples 21 & 22). After stirring at room temperature for two hours, 46.8 mg of sodium triacetoxyborohydride and 4.2 mg of acetic acid are added. The mixture is stirred at room temperature over the weekend (48 hr) (the reaction was also monitored by MS) and the volatile materials are removed under reduced pressure to a residue to which is added 8 ml of 0.5% trifluoroacetic acid in a 1:1 mixture of water and p-dioxane. The reaction mixture is stirred at room temperature for 1.5 hour. The reaction was monitored by MS and the desired product is identified by LC/MS. The reaction mixture is concentrated to about one ml and 18.7 mg (22.3%) of the desired product is separated by preparative HPLC.

Figure 5:
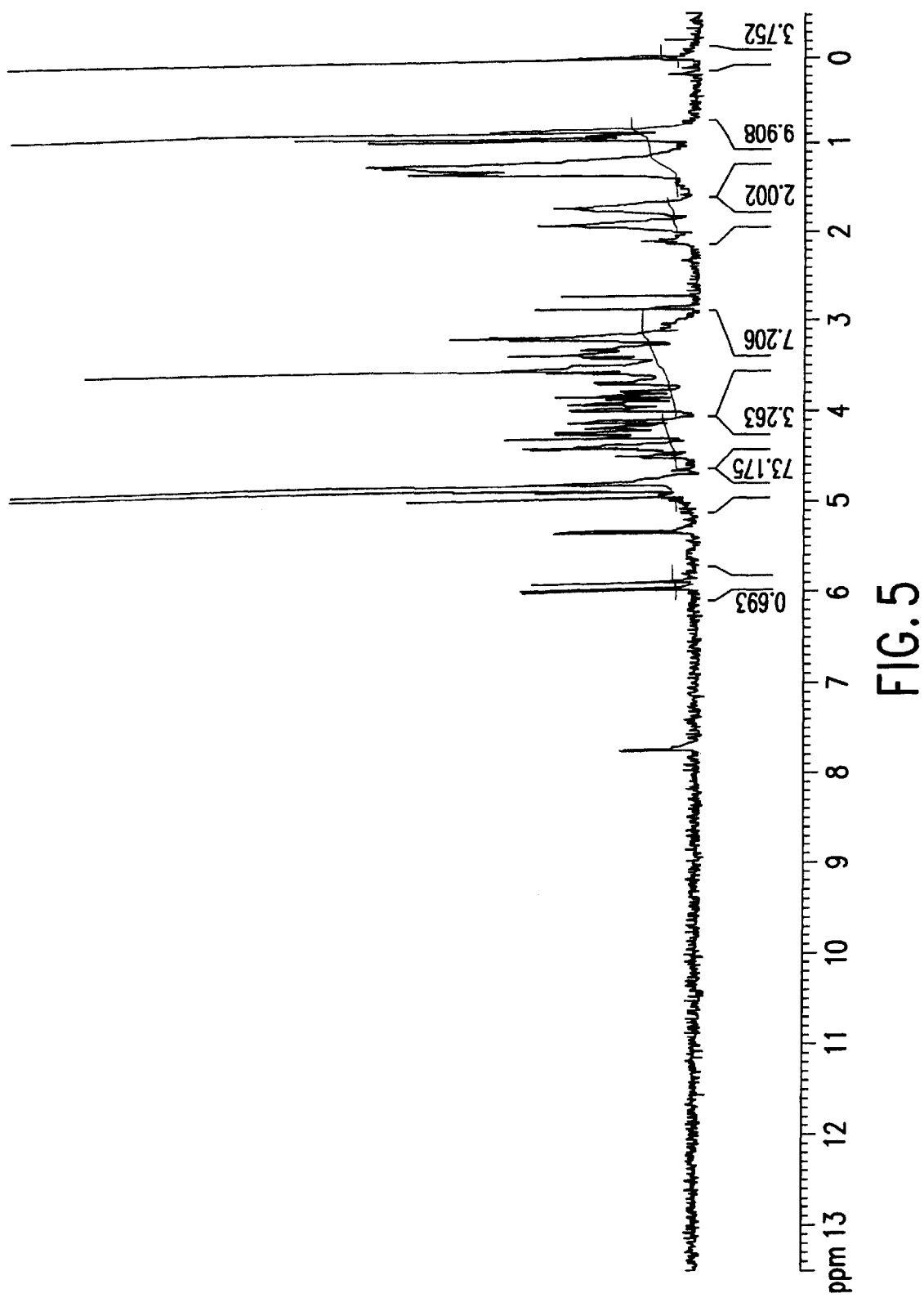
FIG. 5. Proton NMR spectrum of Example 8 in $D_2O$ at 300 MHz

HPLC conditions:
column: Prodigy ODS 4.6×150 mm
mobile phase: gradient, A=0.02% TFA/water; B=0.02% TFA/acetonitrile
flow rate: 1.0 ml/min
detection: 215 nm, MSD
retention time: 5.4 min
Molecular formula: $C_{54}H_{94}N_{12}O_{18}$;
Molecular weight: positive ion electrospray MS m/z= 1199.7 $(M+H)^+$ and 600.7 $(M+2H)^{2+}$; 401.0 $(M+3H)^{3+}$;
Ultraviolet absorption spectrum: $\lambda_{max}$ nm (water)=259;
Proton magnetic resonance spectrum (300 Mhz $D_2O$): FIG. 5.

EXAMPLE 9

16-((R)-{[(3R,4S,5R)-5-(Aminomethyl)-4-hydroxy-3-methoxytetrahydro-2-furanyl]oxy}{(2S,3S,4R, 5R)-5-[2,4-dioxo-3,4-di hydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-15-pentyl-3, 5,8,11,15-pentaazaheptadecane-1,17-dioic Acid The title compound is prepared by the procedure of Example 8, using 56.8 mg (60 μmol) of 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1, 17-dioic acid ($\lambda_{max}$ nm in water=259) in 3.0 ml of methanol, 300 μl of pyridine, 300 μl of 2,4-pentanedione, 15 mg montmorillonite K-10, 18 μl of pentanal and 180 μmol of sodium triacetoxyborohydride to give 21 mg of the desired product.

Figure 6:
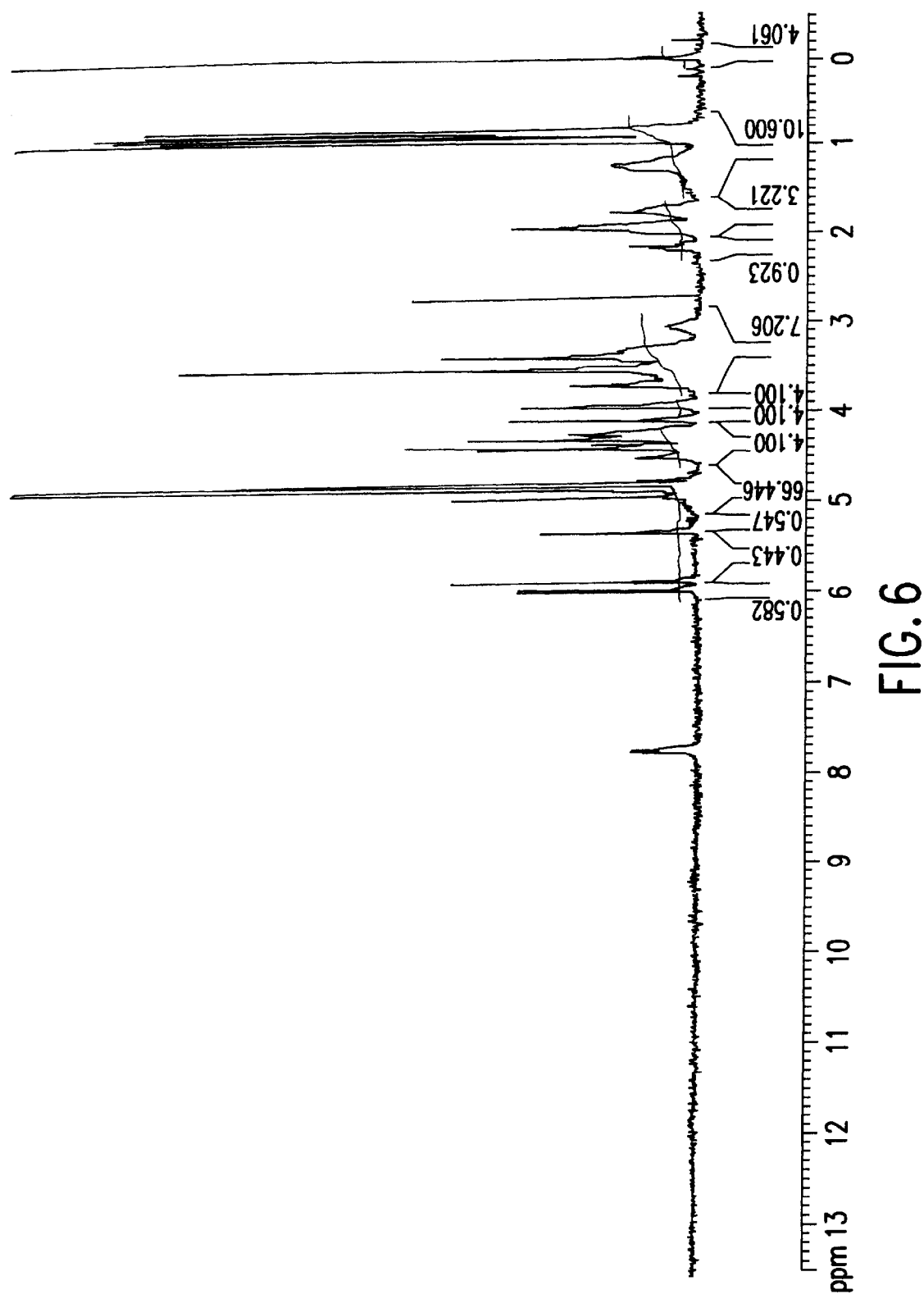
FIG. 6. Proton NMR spectrum of Example 9 in $D_2O$ at 300 MHz

HPLC conditions:
column: Prodigy ODS 4.6×150 mm
mobile phase: gradient, A=0.02% TFA/water; B=0.02% TFA/acetonitrile
flow rate: 1.0 ml/min
detection: 215 nm, MSD
retention time: 5.7 min
Molecular formula: $C_{43}H_{73}N_{11}O_{17}$;
Molecular weight: positive ion electrospray MS m/z= 1018.6 $(M+H)^+$ and 510.1 $(M+2H)^{2+}$;
Proton magnetic resonance spectrum (300 Mhz $D_2O$): FIG. 6;
Ultraviolet absorption spectrum: $\lambda_{max}$ nm (water)=259.

EXAMPLE 10

4-[13-((2R)-2-{[(3R,4S,5R)-5-(Aminomethyl)-4-hydroxy-3-methoxytetrahydro-2-furanyl]oxy}-1-carboxy-2-{(2S,3S,4R,5R)-5-[2,4-dioxo-3,4-dihydro-1 (2H)-pyrimidinyl]-3,4-dihydroxytetrahydro-2-furanyl}ethyl)-26-carboxy-19-(1-hydroxy-2-methylpropyl)-22-(2-iminohexahydro-4-pyrimidinyl) -27-methyl-18,21, 24-trioxo-13,17,20,23,25-pentaazaoctacos-1-yl]-4-methylmorpholin-4-ium The title compound is prepared by the procedure of Example 8, using 198.6 mg (210 μmol) of 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1, 17-dioic acid ($\lambda_{max}$ nm in water=259) in 3.0 ml of methanol, 300 µl of pyridine, 300 µl of 2,4-pentanedione, 15 mg montmorillonite K-10, 18 µl of 4-methyl-4-(12-oxododecyl) morpholin-4-ium (see example 23) and 180 µmol of sodium triacetoxyborohydride to give 26.7 mg of the desired product.

Figure 7:
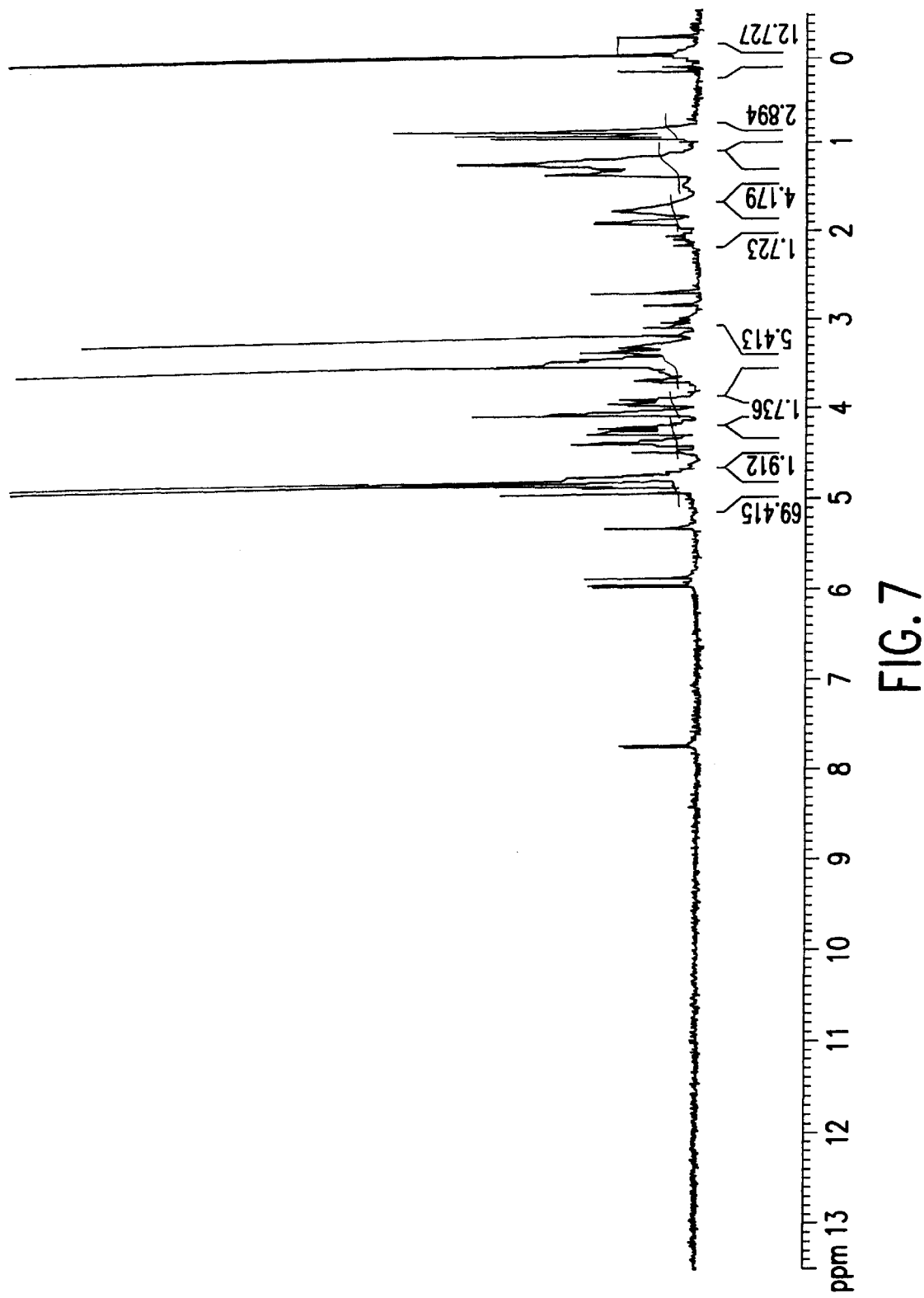
FIG. 7. Proton NMR spectrum of Example 10 in $D_2O$ at 300 MHz

HPLC conditions: column: Prodigy ODS 4.6×150 mm mobile phase: gradient, A=0.02% TFA/water; B=0.02% TFA/acetonitrile flow rate: 1.0 ml/min detection: 215 nm, MSD retention time: 6.3 min Molecular formula: $C_{55}H_{97}IN_{12}O_{18}$;

Molecular weight: positive ion electrospray MS m/z= 809.7 $(2M^++H)^{3+}$ and 607.5 $(M^++H)^{2+}$; 405.5 $(M^++2H)^+$;

Ultraviolet absorption spectrum: $\lambda_{max}$ nm (water)=260;

Proton magnetic resonance spectrum (300 Mhz $D_2O$): FIG. 7.

EXAMPLE 11

14-[5-((R)-{(2S,3S,4R,5R)-5-[2,4-Dioxo-3,4-dihydro-1 (2H)-pyrimidinyl]-3,4-dihydroxytetrahydro-2-furanyl}{[(3R,4S,5R)-4-hydroxy-3-methoxy-5-({[(octylamino)carbonyl]amino}methyl)tetrahydro-2-furanyl]oxy}methyl)-3-octyl-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic Acid To a suspension of 47.3 mg (50 µmol) of 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid ($\lambda_{max}$ nm in water=259) in 4.0 ml of N,N-dimethylformamide is added 20.2 mg (130 µmol) of n-octyl isocyanate at room temperature. The reaction mixture is stirred for 20 hours. The reaction is monitored by MS and checked by LC/MS. The reaction mixture is concentrated to about 1 ml, and the fractions with molecular weights of 1237.9 and 1255.9 are separated by preparative HPLC. After heating the mixture in 5 ml of water at 70° C. for 45 minutes, 27 mg (43.6%) of the desired product (molecular weight= 1237.9) is obtained.

Figure 8:
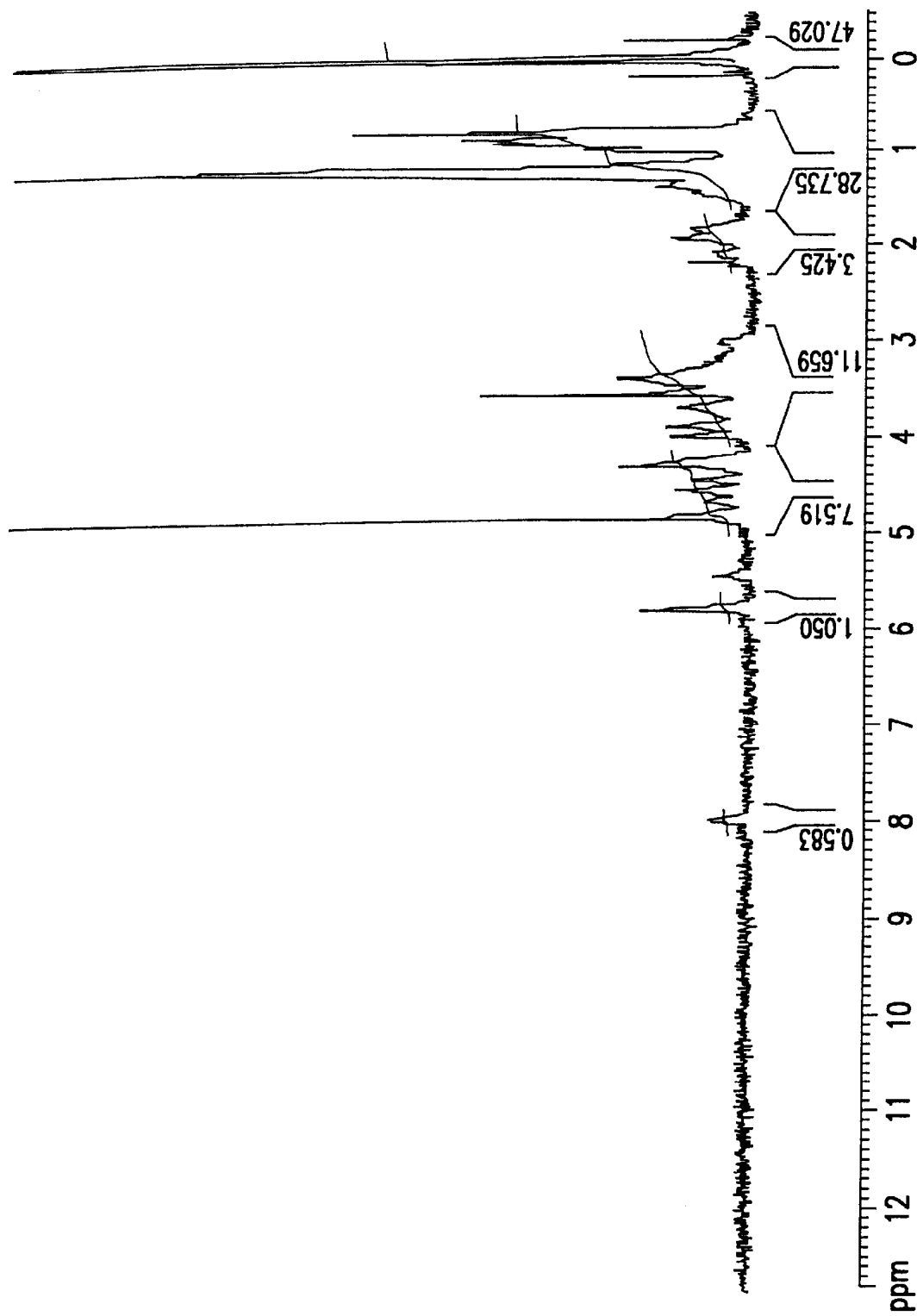
FIG. 8. Proton NMR spectrum of Example 11 in $D_2O$ at 300 MHz

HPLC conditions:

column: Prodigy ODS 4.6×150 mm mobile phase: gradient, A=0.02% TFA/water; B=0.02% TFA/acetonitrile flow rate: 1.0 ml/min detection: 215 nm, MSD Molecular formula: $C_{56}H_{95}N_{13}O_{18}$;

Molecular weight: positive ion electrospray MS m/z= 1238.85 $(M+H)^+$ and 619.86 $(M+2H)^{2+}$;

Ultraviolet absorption spectrum: $\lambda_{max}$ nm (water)=262;

Proton magnetic resonance spectrum (300 Mhz $D_2O$): FIG. 8.

EXAMPLE 12

14-[5-((R)-{(2S,5R)-5-[2,4-Dioxo-3,4-dihydro-1 (2H)-pyrimidinyl]-3,4-dihydroxytetrahydro-2-furanyl}{[(5R)-4-hydroxy-3-methoxy-5-({[(4-fluoroanilino)carbonyl]amino}methyl)tetrahydro-2-furanyl]oxy}methyl)-3-(4-fluorophenyl)-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic Acid The title compound is prepared by the procedure of Example 11, using 47.3 mg (50 µmol) of 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid ($\lambda_{max}$ nm in water=259) and 27.4 mg (200 µmol) 4-methoxyphenyl isocyanate in 4.0 ml of N,N-dimethyl formamide to give 17.3 mg of the desired product.

Figure 9:
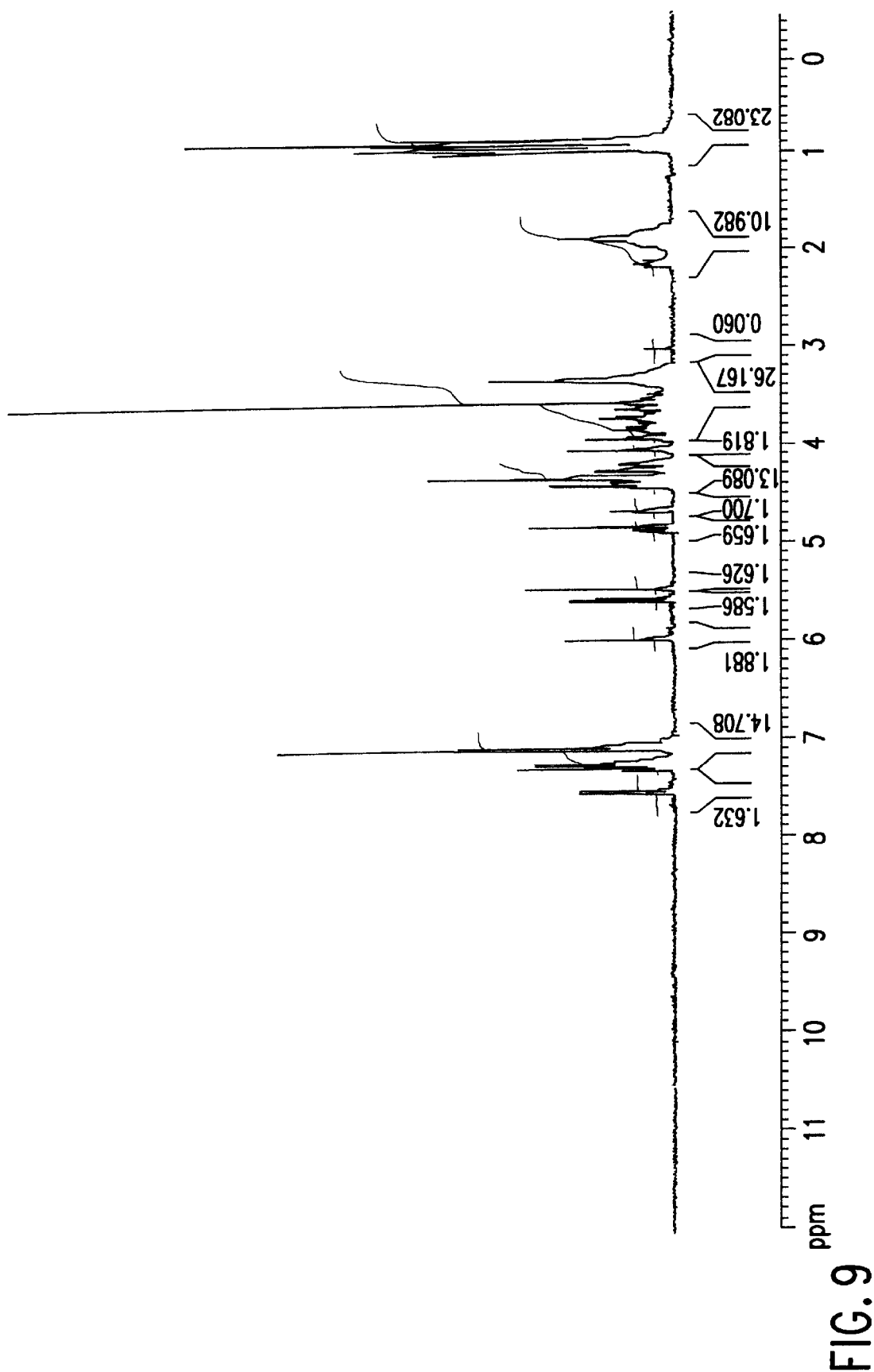
FIG. 9. Proton NMR spectrum of Example 12 in $D_2O$ at 300 MHz

Molecular formula: $C_{52}H_{69}F_2N_{13}O_{18}$;

Molecular weight: positive ion electrospray MS m/z= 1202.7 $(M+H)^+$ and 601.6 $(M+2H)^{2+}$;

Proton magnetic resonance spectrum (300 Mhz $D_2O$): FIG. 9.

EXAMPLE 13

14-[5-((R)-{(2S,5R)-5-[2,4-Dioxo-3,4-dihydro-1 (2H)-pyrimidinyl]-3,4-dihydroxytetrahydro-2-furanyl}{[(5R)-4-hydroxy-3-methoxy-5-({[(4-methoxyanilino)carbonyl]amino}methyl)tetrahydro-2-furanyl]oxy}methyl)-3-(4-methoxyphenyl)-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic Acid The title compound is prepared by the procedure of Example 11, using 47.3 Mg (50 µmol) of 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid ($\lambda_{max}$ nm in water=259) and 14.9 mg (100 µmol) 4-methoxyphenyl isocyanate in 4.0 ml of N,N-dimethyl formamide to give 28.6 mg of the desired product.

Molecular formula: $C_{54}H_{75}IN_{13}O_{20}$;

Molecular weight: positive ion electrospray MS m/z= 1226.7 $(M+H)^+$ and 613.7 $(M+2H)^{2+}$.

EXAMPLE 14

14-[5-((R)-{(2S,3S,4R,5R)-5-[2,4-Dioxo-3,4-dihydro-1 (2H)-pyrimidinyl]-3,4-dihydroxytetrahydro-2-furanyl}{[(3R,4S,5R)-5-({[(hexylamino)carbonyl]amino}methyl)-4-hydroxy-3-methoxytetrahydro-2-furanyl]oxy}methyl)-3-hexyl-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic Acid The title compound is prepared by the procedure of Example 11, using 47.3 mg (50 µmol) of 16-({[5-

(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1, 17-dioic acid ($\lambda_{max}$ nm in water=259) and 16.5 mg (130 $\mu$mol) N-hexyl isocyanate in 4.0 ml of N,N-dimethyl formamide to give 16.4 mg of the desired product.

Figure 10:
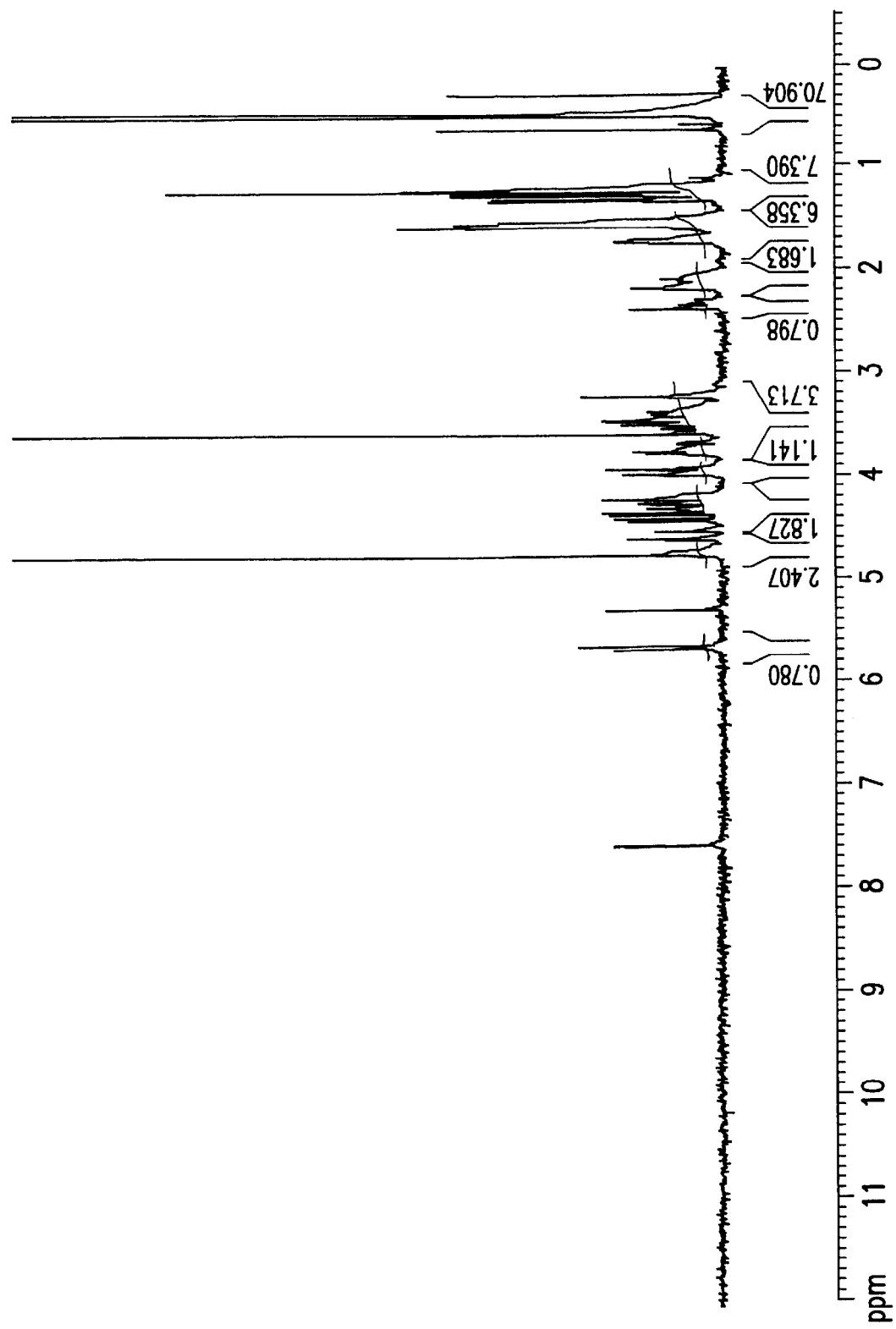
FIG. 10. Proton NMR spectrum of Example 14 in $D_2O$ at 300 MHz

Molecular formula: $C_{52}H_{87}N_{13}O_{18}$;

Molecular weight: positive ion electrospray MS m/z= 1182.6 (M+H)$^+$ and 591.7 (M+2H)$^{2+}$;

Ultraviolet absorption spectrum: $\lambda_{max}$ nm (water)=262;

Proton magnetic resonance spectrum (300 Mhz D$_2$O): FIG. 10.

EXAMPLE 15

14-[5-((R)-{(2S,3S,4R,5R)-5-[2,4-Dioxo-3,4-dihydro-1 (2H)-pyrimidinyl]-3,4-dihydroxytetrahydro-2-furanyl}{[(3R,4S,5R)-5-({[(dodecylamino)carbonyl]amino}methyl)-4-hydroxy-3-methoxytetrahydro-2-furanyl]oxy}methyl)-3-dodecyl-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic Acid The title compound is prepared by the procedure of Example 11, using 56.8 mg (60 $\mu$mol) of 16-({[5-(aminomethyl)-4-hydroxy-3-methoxytetrahydro-2-furanyl]oxy}{5-[2,4-dioxo-3,4-dihydro-1(2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1, 17-dioic acid ($\lambda_{max}$ nm in water=259) and 14.9 mg (100 $\mu$mol) n-dodecyl isocyanate in 4.0 ml of N,N-dimethyl formamide to give 30.0 mg of the desired product.

Molecular formula: $C_{64}H_{111}N_{13}O_{18}$;

Molecular weight: positive ion electrospray MS m/z= 1350.6 (M+H)$^+$ and 675.8 (M+2H)$^{2+}$.

EXAMPLE 16

16-((R)-{(2S,3S,4R,5R)-5-[2,4-Dioxo-3,4-dihydro-1 (2H)-pyrimidinyl]-3,4-dihydroxytetrahydro-2-furanyl}{[(3R,4S,5R)-5-({[(hexadecylamino)carbonyl]amino}methyl)-4-hydroxy-3-methoxytetrahydro-2-furanyl]oxy}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic Acid The title compound is prepared by the procedure of Example 11, using 50.0 mg (52 $\mu$mol) of 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1, 17-dioic acid ($\lambda_{max}$ nm in water=259) and 14.0 mg (52 $\mu$mol) hexadecyl isocyanate in 2.0 ml of N,N-dimethyl formamide to give 3.0 mg of the desired product.

Figure 11:
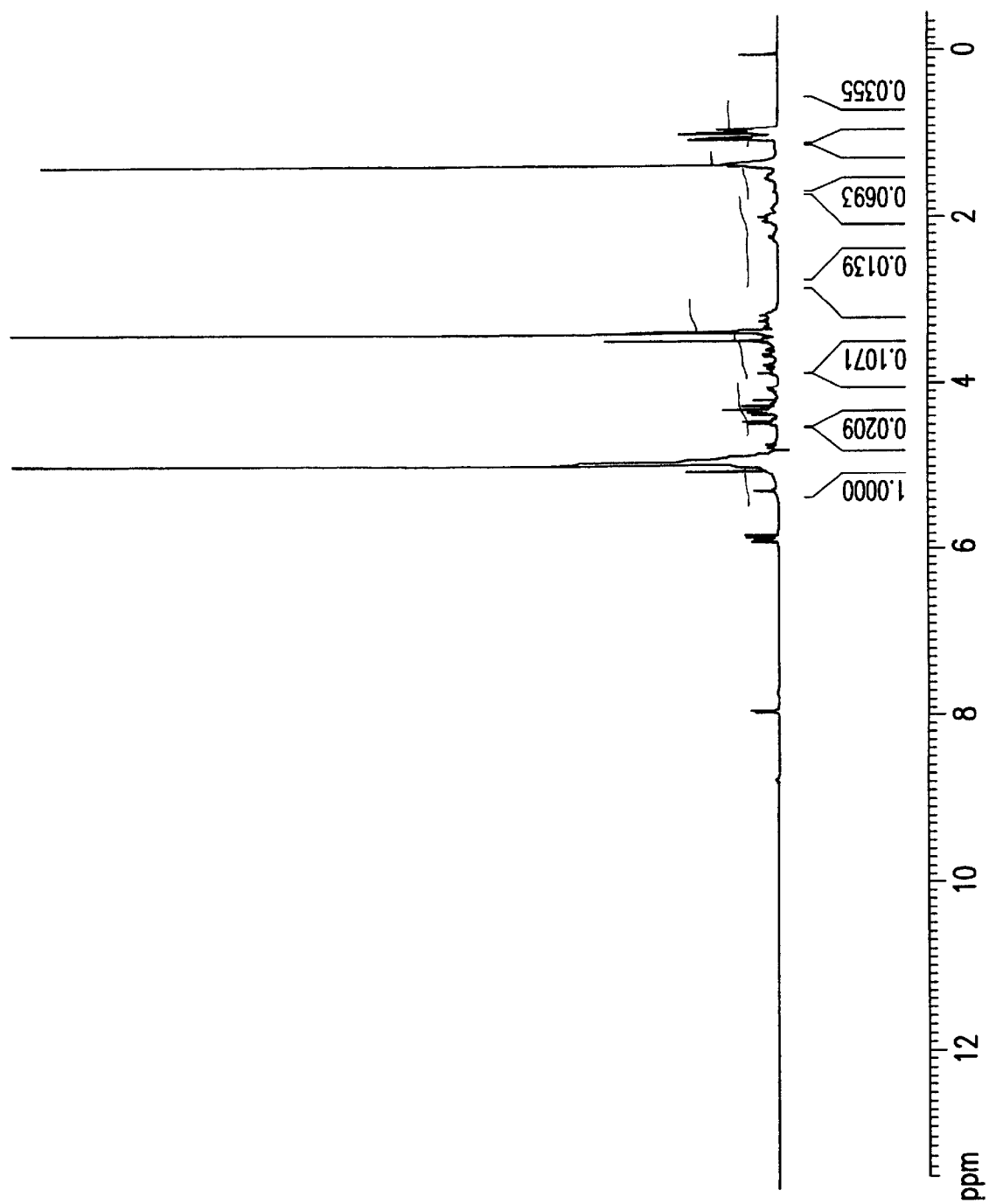
FIG. 11. Proton NMR spectrum of Example 16 in $D_2O$ at 300 MHz

Molecular formula: $C_{55}H_{96}N_{12}O_{18}$;

Molecular weight: positive ion electrospray MS m/z= 1213.5 (M+H)$^+$ and 607.4 (M+2H)$^{2+}$;

Proton magnetic resonance spectrum (300 Mhz D$_2$O): FIG. 11.

EXAMPLE 17

16-[(R)-{(2S,3S,4R,5R)-5-[2,4-Dioxo-3,4-dihydro-1 (2H)-pyrimidinyl]-3,4-dihydroxytetrahydro-2-furanyl}({(3R,4S,5R)-4-hydroxy-3-methoxy-5-[(pentylamino)methyl]tetrahydro-2-furanyl}oxy)methyl]-9-(1-hydroxy-2-methylpropyl)-6-(2-iminohexahydro-4-pyrimidinyl)-2-isopropyl-4,7,10-trioxo-15-pentyl-3,5,8,11,15-pentaazaheptadecane-1, 17-dioic Acid To a solution of 50 mg (53 $\mu$mol) 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1, 17-dioic acid ($\lambda_{max}$ nm in water=259) in 0.4 ml of methanol is added 9.5 mg (2.0 eq., 110 $\mu$mol) of valeraldehyde and 3.3 mg (1.0 eq., 53 $\mu$mol) of sodium cyanoborohydride. After stirring for 5 minutes, 0.04 ml of 1 N methanolic hydrochloric acid is added. The reaction mixture is then stirred for 0.5 hour (the reaction is monitored by MS). The solvent is removed under reduced pressure to give a yellow gum. The desired product is identified by LC/MS and separated by preparative HPLC to give 4.9 mg (9.0% yield) of the desired product as a white solid.

Molecular formula: $C_{48}H_{83}N_{11}O_{17}$;

Molecular weight: positive ion electrospray MS m/z= 1086.7 (M+H)$^+$ and 543.8 (M+2H)$^{2+}$.

EXAMPLE 18

16-[(R)-{(2S,3S,4R,5R)-5-[2,4-Dioxo-3,4-dihydro-1 (2H)-pyrimidinyl]-3,4-dihydroxytetrahydro-2-furanyl}({(3R,4S,5R)-4-hydroxy-3-methoxy-5-[(pentylamino)methyl]tetrahydro-2-furanyl}oxy)methyl]-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic Acid The title compound is prepared by the procedure of Example 17, using 50.0 mg (53 $\mu$mol) of 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1, 17-dioic acid ($\lambda_{max}$ nm in water=259) in 0.4 ml of methanol, 4.7 mg (1.0 eq., 55 $\mu$mol) of valeraldehyde and 3.3 mg (1.0 eq., 53 $\mu$mol) of sodium cyanoborohydride to give 7.0 mg of the desired product.

Figure 12:
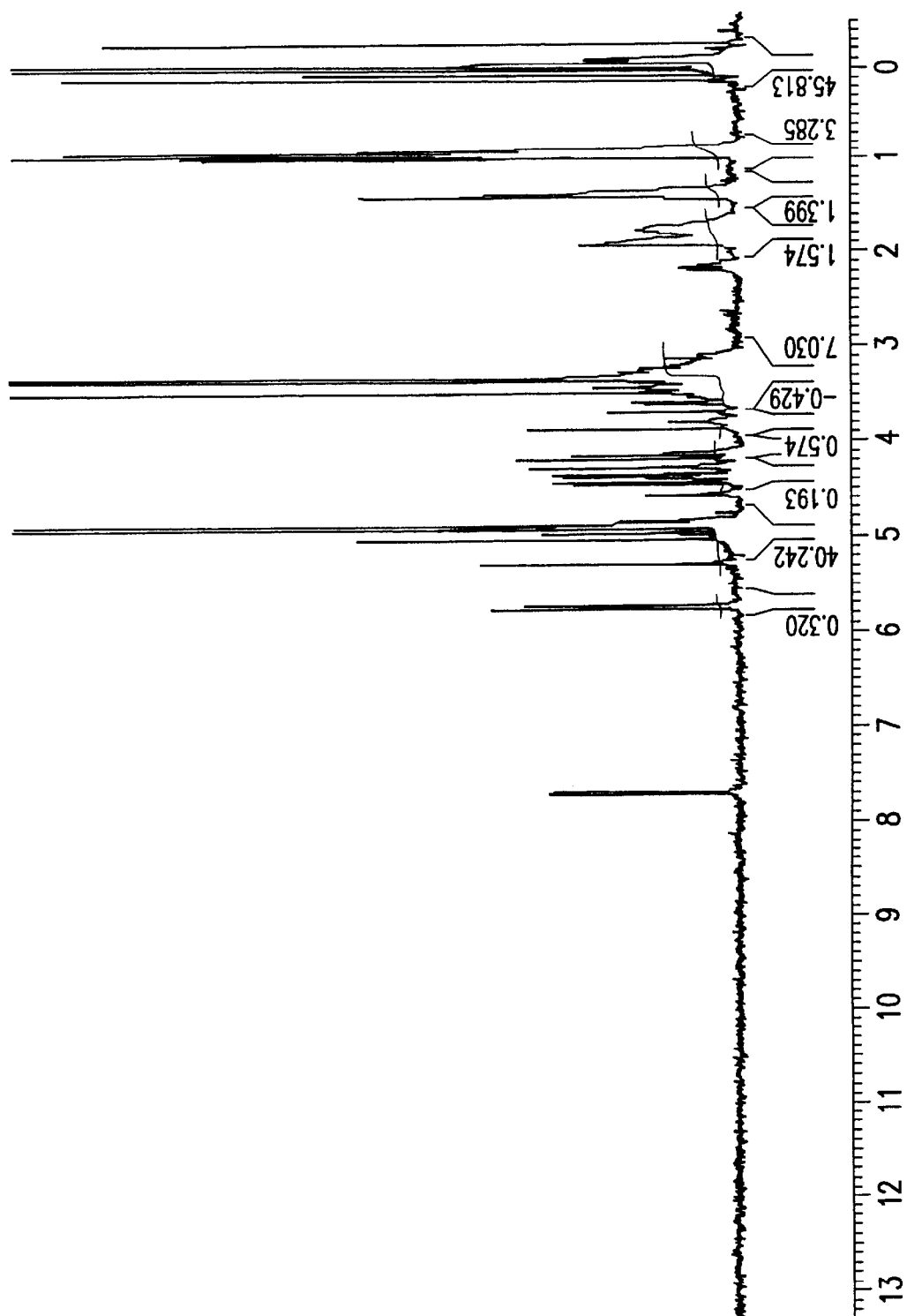
FIG. 12. Proton NMR spectrum of Example 18 in $D_2O$ at 300 MHz

Molecular formula: $C_{43}H_{73}N_{11}O_{17}$;

Molecular weight: positive ion electrospray MS m/z= 1016 (M+H)$^+$ and 508.8 (M+2H)$^{2+}$;

Proton magnetic resonance spectrum (300 Mhz D$_2$O): FIG. 12.

EXAMPLES 19a AND 19b 16-((R)-[((3R,4S,5R)-5-{[([1,1'-Biphenyl]-4-ylmethyl)amino]methyl}-4-hydroxy-3-methoxytetrahydro-2-furanyl)oxy]{(2S,3S,4R,5R)-5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic Acid (Example 19a) and
15-([1,1'-Biphenyl]-4-ylmethyl)-16-((R)-[((3R,4S,5R)-5-{[([1,1'-biphenyl]-4-ylmethyl)amino]methyl}-4-hydroxy-3-methoxytetrahydro-2-furanyl)oxy]{(2S,3S,4R,5R)-5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic Acid (Example 19b)

To a solution of 20 mg (21 μmol) 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid ($\lambda_{max}$ nm in water=259) in 0.4 ml of methanol is added 77 mg (2.0 eq., 42 μmol) of 4-biphenylcarboxaldehyde and 1.3 mg (1.0 eq., 21 μmol) of sodium cyanoborohydride. After stirring for 5 minutes, 0.04 ml of methanolic hydrochloric acid is added. The reaction mixture is then stirred for 0.5 hour and monitored by MS. The solvent is removed under reduced pressure to give a yellow gum. The desired products are separated by preparative HPLC to give 3.0 mg (12% yield) of Example 19a as a white solid and 4.0 mg (15% yield, L17742–171–2) of Example 19b also as a white solid.

Example 19a

Figure 13:
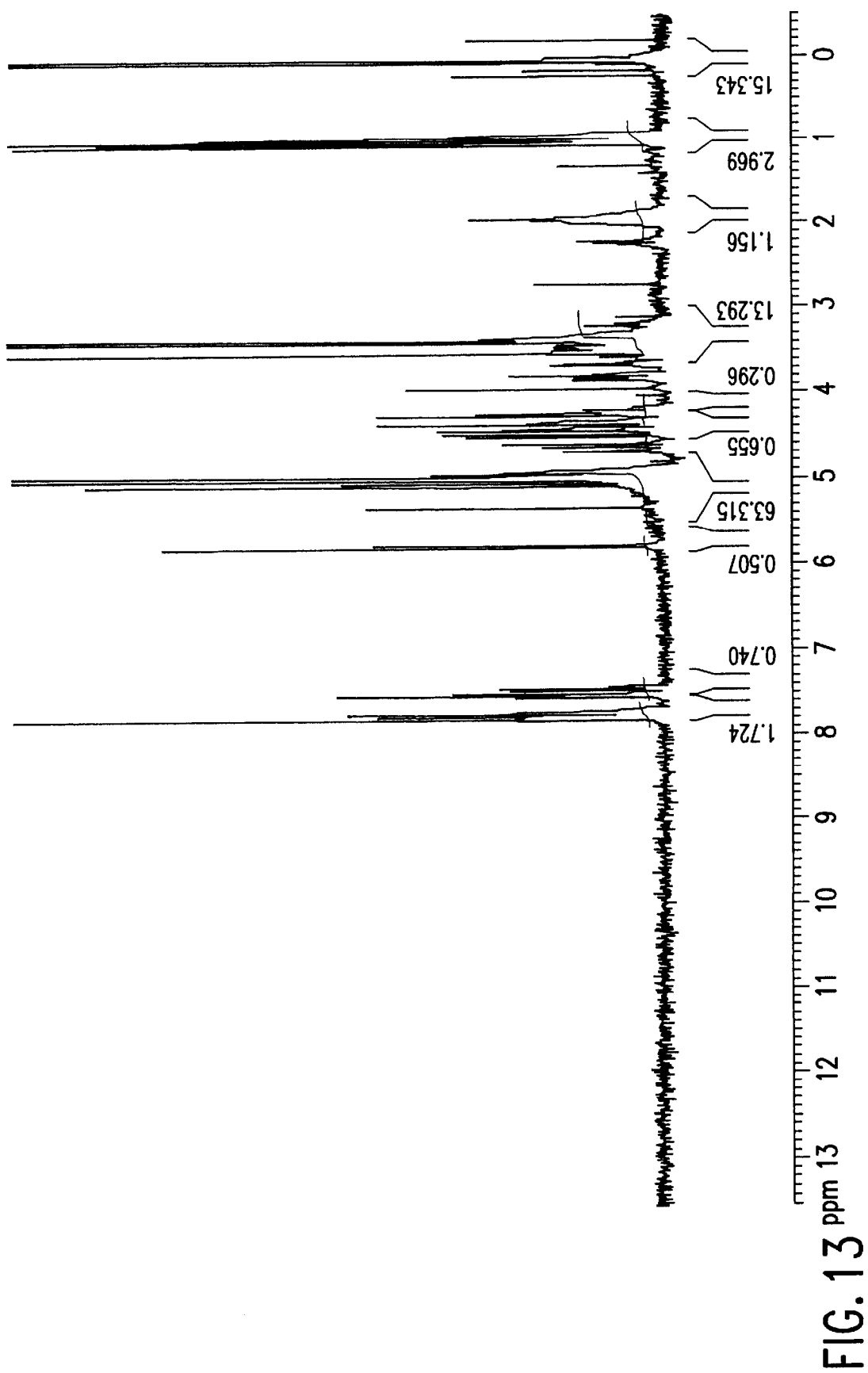
FIG. 13. Proton NMR spectrum of Example 19A in $D_2O$ at 300 MHz

Molecular formula: $C_{51}H_{73}N_{11}O_{17}$;

Molecular weight: positive ion electrospray MS m/z= 1112.5 $(M+H)^+$ and 556.7 $(M+2H)^{2+}$;

Proton magnetic resonance spectrum (300 Mhz $D_2O$): FIG. 13.

Example 19b

Figure 14:
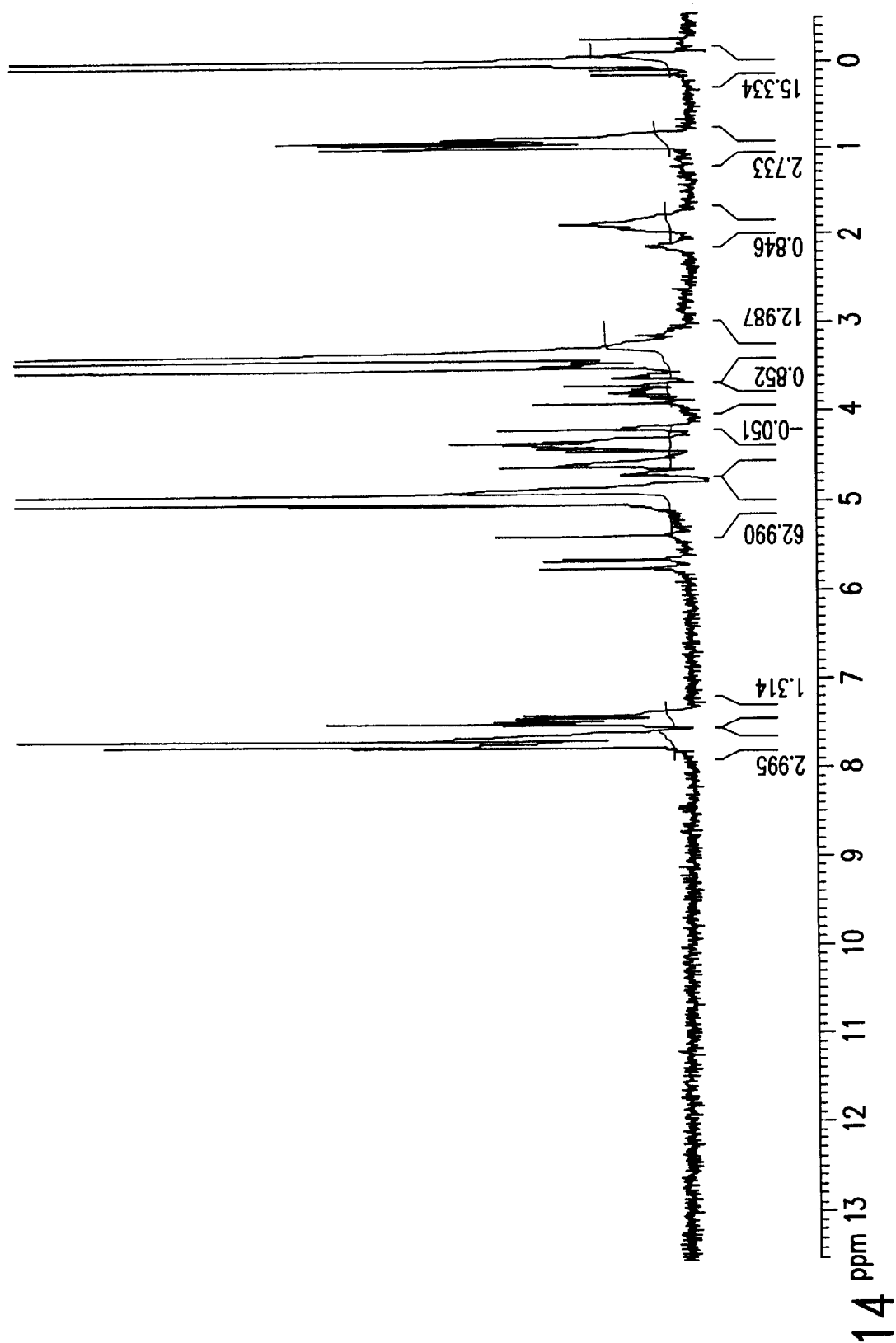
FIG. 14. Proton NMR spectrum of Example 19B in $D_2O$ at 300 MHz

Molecular formula: $C_{64}H_{83}N_{11}O_{17}$;

Molecular weight: positive ion electrospray MS m/z= 1278.7 $(M+H)^+$ and 639.8 $(M+2H)^{2+}$;

Proton magnetic resonance spectrum (300 Mhz $D_2O$): FIG. 14.

EXAMPLE 20a and 20b 16-((R)-({(3R,4S,5R)-5-[(Benzylamino)methyl]-4-hydroxy-3-methoxytetrahydro-2-furanyl}oxy){(2S,3S,4R,5R)-5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid (Example 20a) and
15-Benzyl-16-((R)-({(3R,4S,5R)-5-[(benzylamino)methyl]-4-hydroxy-3-methoxytetrahydro-2-furanyl}oxy){(2S,3S,4R,5R)-5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic Acid (Example 20b)

To a solution of 50 mg (53 μmol) 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid ($\lambda_{max}$ nm in water=259) in 0.4 ml of methanol is added 11 mg (2.0 eq., 106 μmol) of benzaldehyde and 3.3 mg (1.0 eq., 53 μmol) of $NaBH_3CN$. After stirring for 5 minutes, 0.04 ml of methanolic hydrochloric acid is added. The reaction mixture is then stirred for 0.5 hour. The reaction is monitored by MS. The solvent is removed under reduced pressure to give a yellow gum. The desired products are separated by preparative HPLC to give 15 mg (26% yield) of Example 20a as a white solid and 2.5 mg (4% yield) of Example 20b as a white solid.

Example 20a

Figure 15:
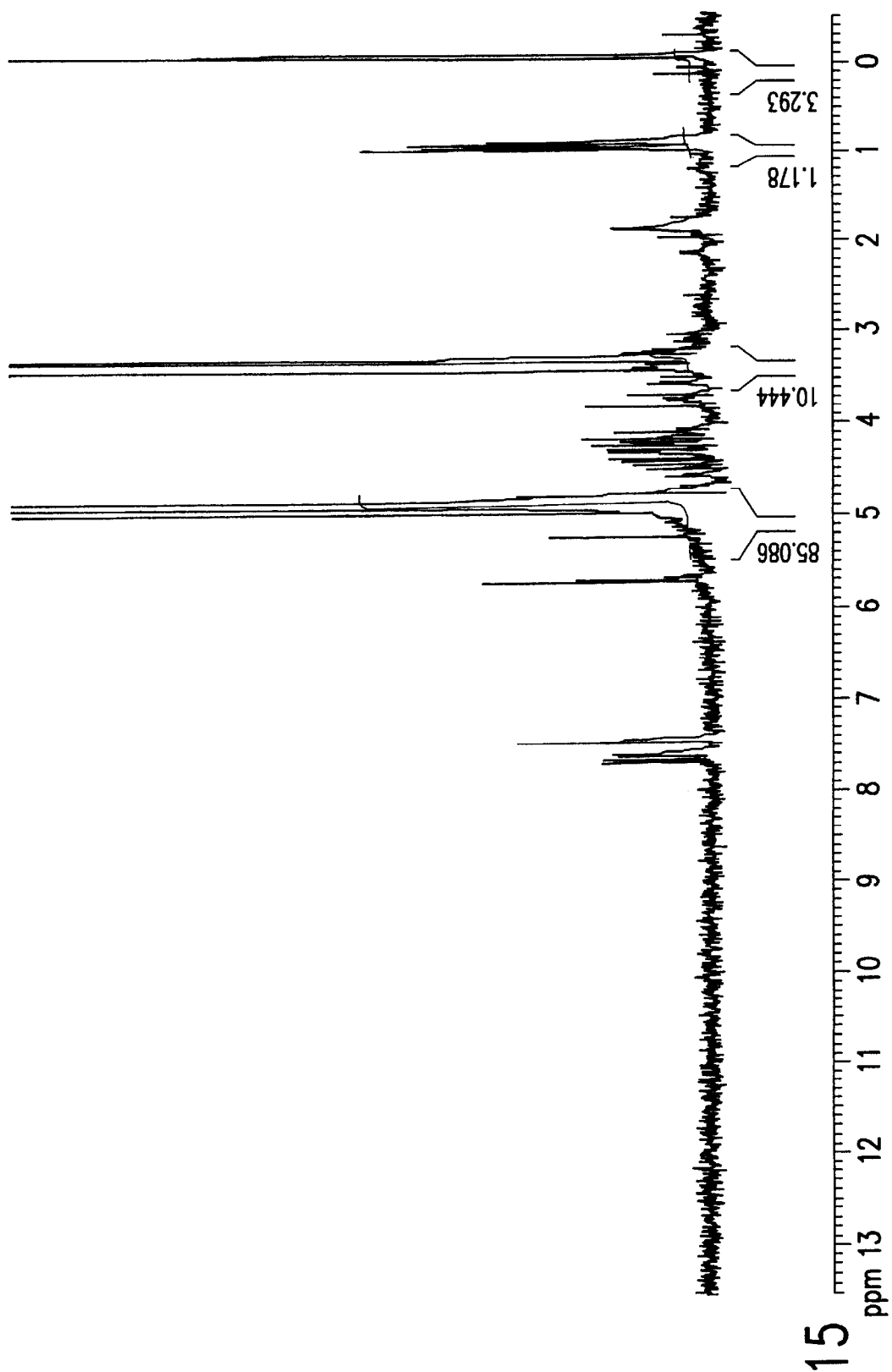
FIG. 15. Proton NMR spectrum of Example 20A in $D_2O$ at 300 MHz

Molecular formula: $C_{45}H_{69}N_{11}O_{17}$;

Molecular weight: positive ion electrospray MS m/z= 1036.1 $(M+H)^+$ and 518.9 $(M+2H)^{2+}$;

Proton magnetic resonance spectrum (300 Mhz $D_2O$): FIG. 15.

Example 20b

Figure 16:
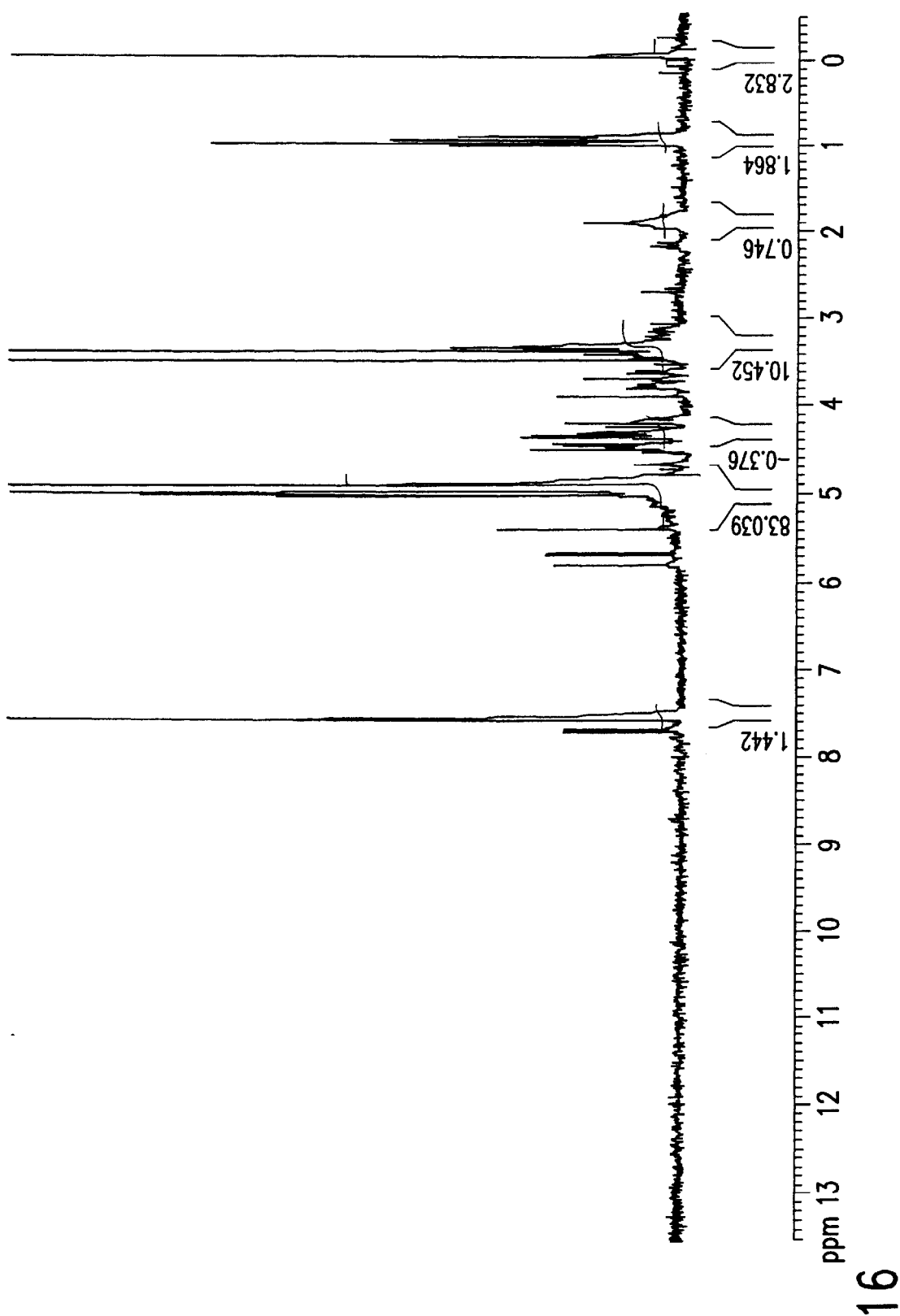
FIG. 16 Proton NMR spectrum of Example 20B in $D_2O$ at 300 MHz

Molecular formula: $C_{52}H_{75}N_{11}O_{17}$;

Molecular weight: positive ion electrospray MS m/z= 1126.5 $(M+H)^+$ and 563.8 $(M+2H)^{2+}$;

Proton magnetic resonance spectrum (300 Mhz $D_2O$): FIG. 16.

EXAMPLE 21

12-(4-Morpholinyl)-1-dodecanol

To a solution of 5.30 g (20 mmol) of 12-bromo-1-dodecanol in 100 ml of acetonitrile is added dropwise 6 ml (68.6 mmol) of morpholine at 0° C. The solution is then stirred at room temperature overnight and filtered. After removal of the acetonitrile, the residue is dissolved in 250 ml of dichloromethane. The dichloromethane solution is washed with water, dried over magnesium sulfate and filtered. The dichloromethane is removed under reduced pressure and the residue is purified by silica gel column chromatography to give 4.2 g (79.2%) of 12-(4-morpholinyl)-1-dodecanol.

Molecular formula: $C_{16}H_{33}NO_2$;

Proton magnetic resonance spectrum (300 Mhz $CH_3Cl$): 3.72 (t, 4H, J=4.6 Hz); 3.66 (t, 2H, J=6.5 Hz); 2.43 (t, 4H, J=4.5 Hz); 2.34 (t, 2H, J=6.9 Hz); 1.50 (m, 21H);

Molecular weight: positive ion electrospray MS m/z= 272.4 $(M+H)^+$;

Elemental analysis: theory, C 70.80; H 12 25; N 5.16; found, C 71.12; H 12.32; N 5.11.

EXAMPLE 22

12-(4-Morpholinyl)-1-dodecanal

A mixture of 542.9 mg (2.0 mmol) of 12-(4-morpholinyl)-1-dodecanol and 3.0 g of (5.10 mmol) of bis(trimethylsilyl) chromate (M. Heravi, Monatsh. Chem. 1998, 129(12), 1305–1308) in 10 ml of dichloromethane is stirred at room temperature overnight and filtered. After removal of the dichloromethane, the residue is purified by silica gel column chromatography to give 210 mg (39%) of 12-(4-morpholinyl)-1-dodecanal.

Molecular formula: $C_{16}H_{31}NO_2$;

Proton magnetic resonance spectrum (300 Mhz $CH_3Cl$): 9.76 (t, 1H, J=1.9 Hz); 3.72 (t, 4H, J=4.7 Hz); 2.43 (t, 4H, J=4.5 Hz); 2.29 (t, 2H, J=5.3 Hz); 1.50 (m, 20H);

Molecular weight: positive ion electrospray MS m/z= 270.3 $(M+H)^+$.

EXAMPLE 23

4-Methyl-4-(12-oxododecyl)morpholin-4-ium

A mixture of 1.0 g (3.7 mmol) of 12-(4-morpholinyl)-1-dodecanal and 4.26 g of (1.86 ml; 30 mmol) of iodomethane in 20 ml of diethyl ether is stirred at room temperature overnight. 4-Methyl-4-(12-oxododecyl)morpholin-4-ium which precipitated from the solution is collected by filtration, washed with diethyl ether and dried to give 259 mg of the desired product.

Molecular formula: $C_{17}H_{34}NO_2$;

Molecular weight: positive ion electrospray MS m/z= 284.4 $M^+$.

EXAMPLE 24

16-((R)-({(3R,4S,5R)-5-[(Acetamido)methyl]-4-hydroxy-3-methoxytetrahydro-2-furanyl}oxy){(2S,3S,4R,5R)-5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic Acid A suspension of 39.0 mg (41.2 µmol) of 16-({[5-(aminomethyl)-4-hydroxy-3-methoxytetrahydro-2-furanyl]oxy}{5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid in 2.0 ml of acetic anhydride is placed in an ultrasonic bath (Branson 1200) at room temperature for 35 minutes. Water (2 ml) and n-butanol (2 ml) are added to the reaction mixture and the volatile materials removed under reduced pressure to a residue which is suspended in 2 ml of acetone and the suspension filtered through glass wool. The desired product (the acetone insoluble product) is recovered as a white solid by dissolving in 2 ml water followed by lyophylization.

Figure 17:
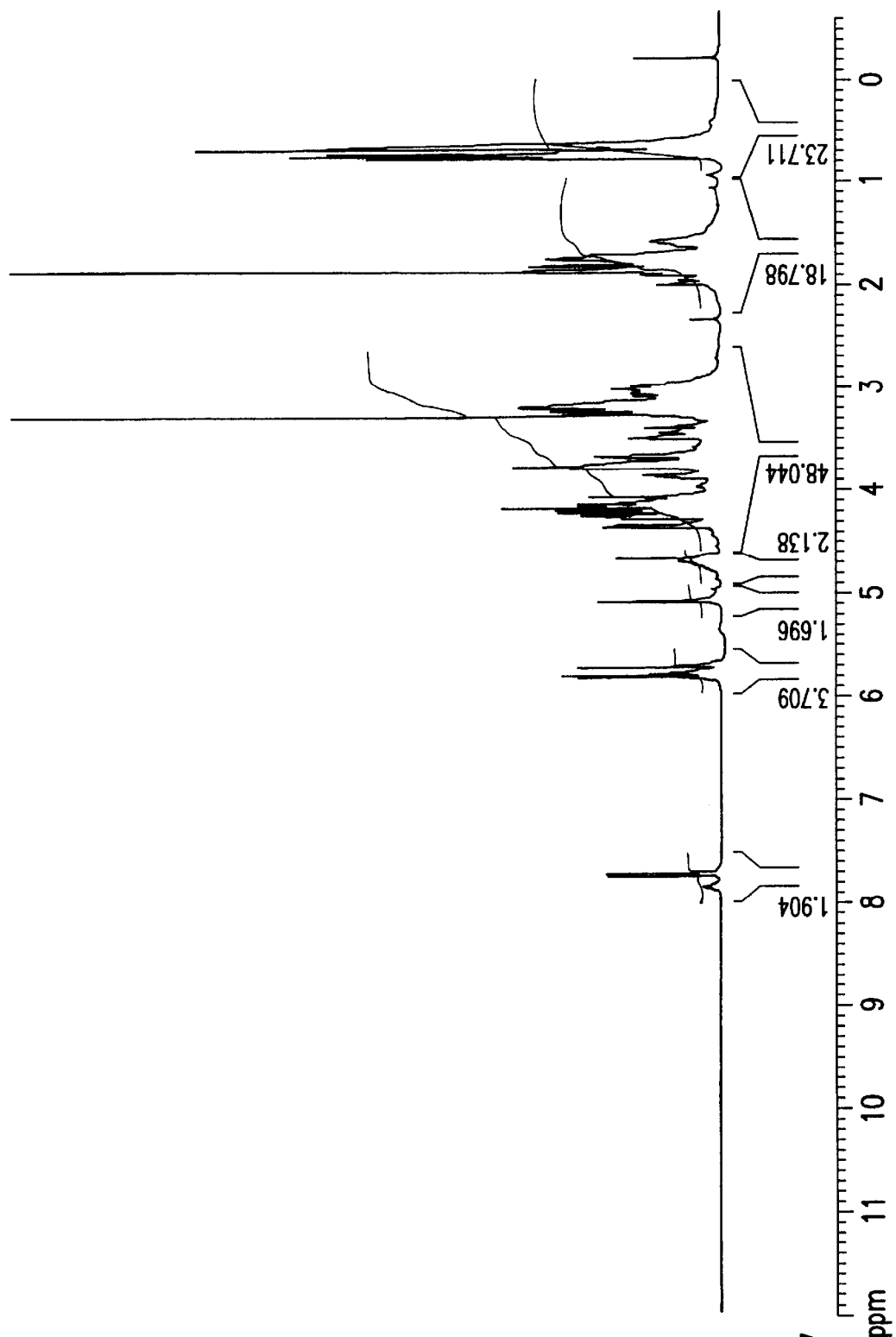
FIG. 17 Proton NMR spectrum of Example 24 in $D_2O$ at 300 MHz

Molecular formula: $C_{40}H_{65}N_{11}O_{18}$;

Molecular weight: positive ion electrospray MS m/z= 988.4 $(M+H)^+$ and 494.7 $(M+2H)^{2+}$;

Proton magnetic resonance spectrum (300 MHz $D_2O$): FIG. 17.

We claim:
1. A compound of the formula:

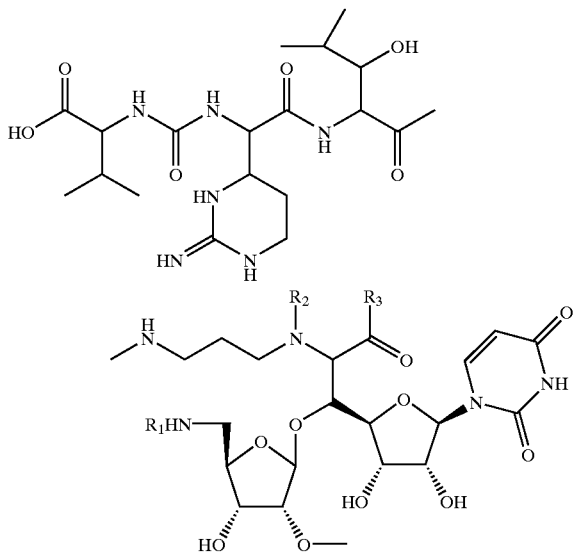

wherein:
$R_1$ is H, aryl, alkyl ($C_1$–$C_{20}$), —$CH_2$-aryl, —C(O)alkyl ($C_1$–$C_{20}$), —C(O)NHalkyl($C_1$–$C_{20}$), or —C(O)NHaryl;

$R_2$ is H, alkyl ($C_1$–$C_{20}$), —$CH_2$aryl, alkyl ($C_1$–$C_{20}$) or —C(O)alkyl($C_1$–$C_{20}$);

$R_3$ is —OH;

$R_2$ and $R_3$ may optionally be taken together to form a moiety

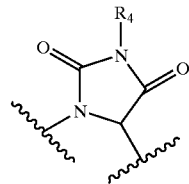

$R_4$ is alkyl ($C_1$–$C_{20}$), or aryl;
provided $R_1$ and $R_2$ are not H when $R_3$ is —OH
or a pharmaceutically acceptable salt thereof.

2. A compound according to claim 1 wherein:
$R_2$ is H, alkyl ($C_1$–$C_{12}$), or —$CH_2$aryl.

3. A compound according to claim 1 wherein:
$R_1$ is H, —C(O)alkyl($C_1$–$C_{16}$), or —C(O)aryl when $R_2$ and $R_3$ are taken together to form a moiety

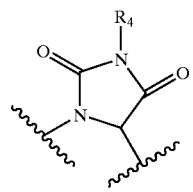

4. A compound according to claim 1 wherein:
$R_4$ is alkyl($C_1$–$C_{16}$), or aryl.

5. The compound according to claim 1 which is 4-[5-((R)-{[(3R,4S,5R)-5-(Aminomethyl)-4-hydroxy-3- methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-3-(4-fluorophenyl)-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid.

6. The compound according to claim 1 which is 14-[5-((R)-{[(3R,4S,5R)-5-(Aminomethyl)-4-hydroxy-3-methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-2,4-dioxo-3-pentyl-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid.

7. The compound according to claim 1 which is 14-[5-((R)-{[(3R,4S,5R)-5-(Aminomethyl)-4-hydroxy-3-methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-3-hexyl-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid.

8. The compound according to claim 1 which is 14-[5-((R)-{[(3R,4S,5R)-5-(Aminomethyl)-4-hydroxy-3-methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-3-(4-methoxyphenyl)-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid.

9. The compound according to claim 1 which is 14-[5-((R)-{[(3R,4S,5R)-5-(Aminomethyl)-4-hydroxy-3-methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-3-dodecyl-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid.

10. The compound according to claim 1 which is 16-((R)-{[(3R,4S,5R)-5-(Aminomethyl)-4-hydroxy-3-methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-15-4,7,10-trioxo-3,5,8,11,15-pentaazaheptadecane-1,17-dioic acid.

11. The compound according to claim 1 which is 16-((R)-{[(3R,4S,5R)-dioxo-3,4-dihydro-1 (2H)-pyrimidinyl]-3,4-dihydroxytetrahydro-2-furanyl}methyl)-15-dodecyl-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid.

12. The compound according to claim 1 which is 16-((R)-{[(3R,4S,5R)-5-(Aminomethyl)-4-hydroxy-3-methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-15-[12-(4-morpholinyl)dodecyl]-4,7,10-trioxo-3,5,8,11,15-pentaazaheptadecane-1,17-dioic acid.

13. The compound according to claim 1 which is 16-((R)-{[(3R,4S,5R)-5-(Aminomethyl)-4-hydroxy-3-methoxytetrahydro-2-furanyl]oxy}{(2S,3S,4R,5R)-5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-15-pentyl-3,5,8,11,15-pentaazaheptadecane-1,17-dioic acid.

14. The compound according to claim 1 which is 4-[13-((2R)-2-{[(3R,4S,5R)-5-(Aminomethyl)-4-hydroxy-3-methoxytetrahydro-2-furanyl]oxy}-1-carboxy-2-{(2S,3S,4R,5R)-5-[2,4-dioxo-3,4-dihydro-1 (2H)-pyrimidinyl]-3,4-dihydroxytetrahydro-2-furanyl}ethyl)-26-carboxy-19-(1-hydroxy-2-methylpropyl)-22-(2-iminohexahydro-4-pyrimidinyl)-27-methyl-18,21,24-trioxo-13,17,20,23,25-pentaazaoctacos-1-yl]-4-methylmorpholin-4-ium.

15. The compound according to claim 1 which is 14-[5-((R)-{(2S,3S,4R,5R)-5-[2,4-Dioxo-3,4-dihydro-1 (2H)-pyrimidinyl]-3,4-dihydroxytetrahydro-2-furanyl}{[(3R,4S,5R)-4-hydroxy-3-methoxy-5-({[(octylamino)carbonyl]amino}methyl)tetrahydro-2-furanyl]oxy}methyl)-3-octyl-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid.

16. The compound according to claim 1 which is 14-[5-((R)-{(2S,5R)-5-[2,4-Dioxo-3,4-dihydro-1 (2H)-pyrimidinyl]-3,4-dihydroxytetrahydro-2-furanyl}{[(5R)-4-hydroxy-3-methoxy-5-({[(4-fluoroanilino)carbonyl]amino}methyl)tetrahydro-2-furanyl]oxy}methyl)-3-(4-fluorophenyl)-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid.

17. The compound according to claim 1 which is 14-[5-((R)-{(2S,5R)-5-[2,4-Dioxo-3,4-dihydro-1 (2H)-pyrimidinyl]-3,4-dihydroxytetrahydro-2-furanyl}{[(5R)-4-hydroxy-3-methoxy-5-({[(4-methoxyanilino)carbonyl]amino}methyl)tetrahydro-2-furanyl]oxy}methyl)-3-(4-methoxyphenyl)-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid.

18. The compound according to claim 1 which is 14-[5-((R)-{(2S,3S,4R,5R)-5-[2,4-Dioxo-3,4-dihydro-1 (2H)-pyrimidinyl]-3,4-dihydroxytetrahydro-2-furanyl}{[(3R,4S,5R)-5-({[(hexylamino)carbonyl]amino}methyl)-4-hydroxy-3-methoxytetrahydro-2-furanyl]oxy}methyl)-3-hexyl-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid.

19. The compound according to claim 1 which is 14-[5-((R)-{(2S,3S,4R,5R)-5-[2,4-Dioxo-3,4-dihydro-1 (2H)-pyrimidinyl]-3,4-dihydroxytetrahydro-2-furanyl}{[(3R,4S,5R)-5-({[(dodecylamino)carbonyl]amino}methyl)-4-hydroxy-3-methoxytetrahydro-2-furanyl]oxy}methyl)-3-dodecyl-2,4-dioxo-1-imidazolidinyl]-9-(1-hydroxy-2-methylpropyl)-6-(2-iminohexahydro-4-pyrimidinyl)-2-isopropyl-4,7,10-trioxo-3,5,8,11-tetraazatetradecan-1-oic acid.

20. The compound according to claim 1 which is 16-((R)-{(2S,3S,4R,5R)-5-[2,4-Dioxo-3,4-dihydro-1 (2H)-pyrimidinyl]-3,4-dihydroxytetrahydro-2-furanyl}{[(3R,4S,5R)-furanyl]oxy}methyl)-9-(1-hydroxy-2-methylpropyl)-6-

(2-iminohexahydro-4-pyrimidinyl)-2-isopropyl-4,7,10-trioxo-3,5,8,11,15-pentaazaheptadecane-1,17-dioic acid.

21. The compound according to claim 1 which is 16-[(R)-{(2S,3S,4R,5R)-5-[2,4-Dioxo-3,4-dihydro-1 (2H)-pyrimidinyl]-3,4-dihydroxytetrahydro-2-furanyl}({(3R,4S,5R)-4-hydroxy-3-methoxy-5-[(pentylamino)methyl] tetrahydro-2-furanyl}oxy)methyl]-9-(1-hydroxy-2-methylpropyl)-6-(2-iminohexahydro-4-pyrimidinyl)-2-isopropyl-4,7,10-trioxo-15-pentyl-3,5,8,11,15-pentaazaheptadecane-1,17-dioic acid.

22. The compound according to claim 1 which is 16-[(R)-{(2S,3S,4R,5R)-5-[2,4-Dioxo-3,4-dihydro-1 (2H)-pyrimidinyl]-3,4-dihydroxytetrahydro-2-furanyl}({(3R,4S,5R)-4-hydroxy-3-methoxy-5-[(pentylamino)methyl] tetrahydro-2-furanyl}oxy)methyl]-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid.

23. The compound according to claim 1 which is 16-((R)-[((3R,4S,5R)-5-{[([1,1'-Biphenyl]-4-ylmethyl)amino] methyl}-4-hydroxy-3-methoxytetrahydro-2-furanyl)oxy]{(2S,3S,4R,5R)-5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid.

24. The compound according to claim 1 which is 15-([1,1'-Biphenyl]-4-ylmethyl)-16-((R)-[((3R,4S,5R)-5-{[([1,1'-biphenyl]-4-ylmethyl)amino]methyl}-4-hydroxy-3-methoxytetrahydro-2-furanyl)oxy]{(2S,3S,4R,5R)-5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid.

25. The compound according to claim 1 which is 16-((R)-({(3R,4S,5R)-5-[(Benzylamino)methyl]-4-hydroxy-3-methoxytetrahydro-2-furanyl}oxy){(2S,3S,4R,5R)-5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid.

26. The compound according to claim 1 which is 15-Benzyl-16-((R)-({(3R,4S,5R)-5-[(benzylamino)methyl]-4-hydroxy-3-methoxytetrahydro-2-furanyl}oxy){(2S,3S,4R,5R)-5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid.

27. The compound according to claim 1 which is 16-((R)-({(3R,4S,5R)-5-[(Acetamido)methyl]-4-hydroxy-3-methoxytetrahydro-2-furanyl}oxy){(2S,3S,4R,5R)-5-[2,4-dioxo-3,4-dihydro-1 (2H)-pyrimidinyl]-3,4-dihydroxytetrahydro-2-furanyl}methyl)-9-(1-hydroxy-2-methylpropyl)-6-(2-iminohexahydro-4-pyrimidinyl)-2-isopropyl-4,7,10-trioxo-3,5,8,11,15-pentaazaheptadecane-1,17-dioic acid.

28. A method for treating bacterial infections in warm blooded animals which comprises providing to said animals an antibacterially effective amount of a compound according to claim 1.

29. A pharmaceutical composition which comprises a compound according to claim 1 in association with a pharmaceutically acceptable carrier.

30. A process for the preparation of an AA-896 antibiotic of the formula

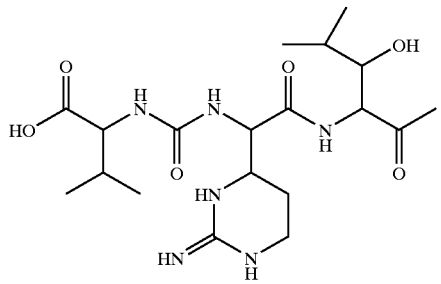

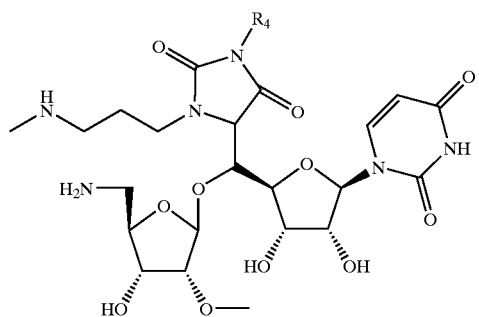

where $R_4$ is alkyl ($C_1$–$C_{20}$), or aryl;

which comprises:

a. protecting the primary amine of

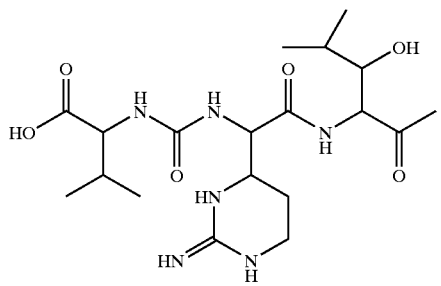

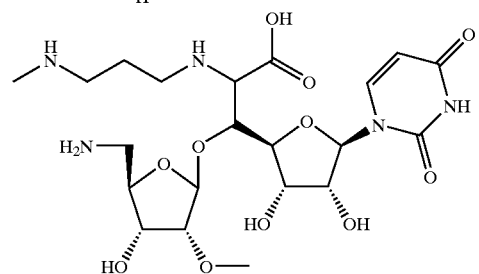

with 2,4-pentanedione in pyridine:methanol to form a protected amine;
b. reacting the secondary amine with an isocyanate, $R_4NCO$; and
c. removal of the primary amine protecting group with aqueous trifluoroacetic acid to form an AA-896 antibiotic.

31. A process for the preparation of an AA-896 antibiotic of the formula

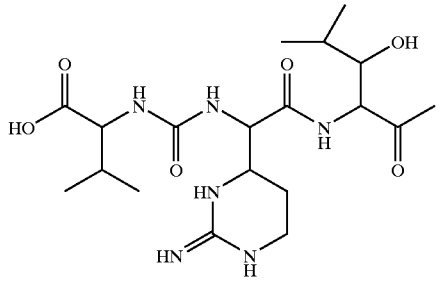

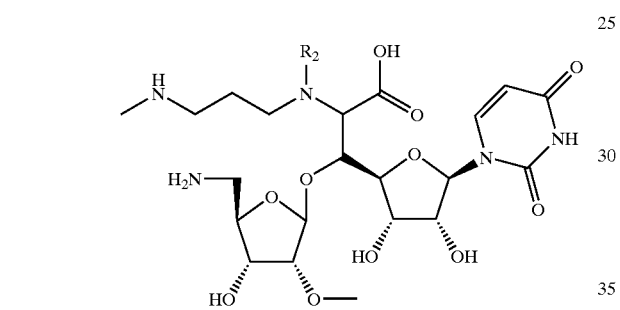

where
  $R_2$ is alkyl ($C_1$–$C_{12}$), or —$CH_2$aryl;
which comprises:
  a. protecting the primary amine of

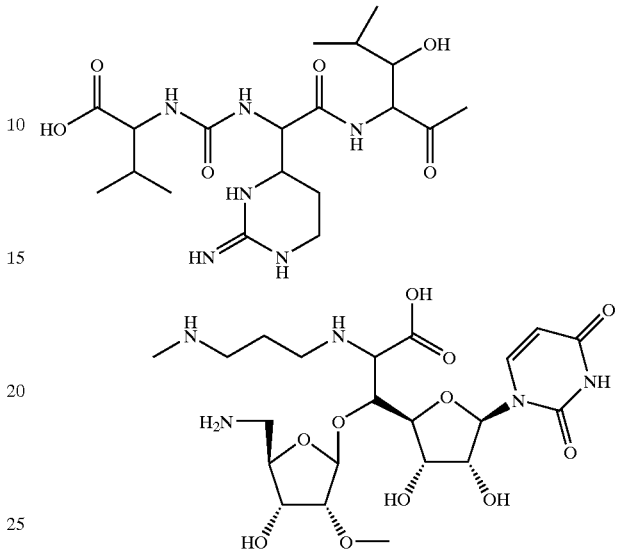

with 2,4-pentanedione in pyridine:methanol to form a protected amine;
b. reacting the secondary amine with an aldehyde, $R_4CH{=}O$ in the presence of a reducing agent such as sodium cyanoborohydride or sodium triacetoxyborohydride; and
c. removal of the primary amine protecting group with aqueous trifluoroacetic acid to form an AA-896 antibiotic.

* * * * *

UNITED STATES PATENT AND TRADEMARK OFFICE
CERTIFICATE OF CORRECTION

PATENT NO. : 6,727,232 B2
DATED : April 27, 2004
INVENTOR(S) : Yang-I Lin et al.

It is certified that error appears in the above-identified patent and that said Letters Patent is hereby corrected as shown below:

<u>Title page,</u>
Item [57], ABSTRACT, delete the structures

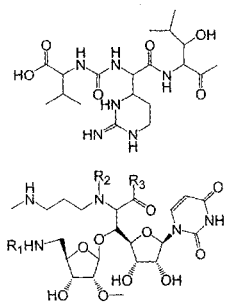   and insert the structure   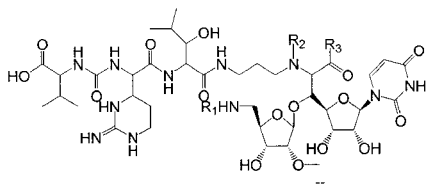

"

<u>Column 2,</u>
Lines 3-25, delete the structures

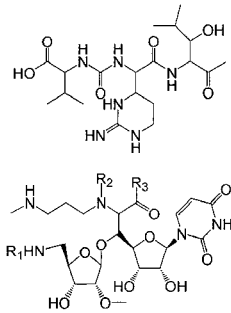   and insert the structure   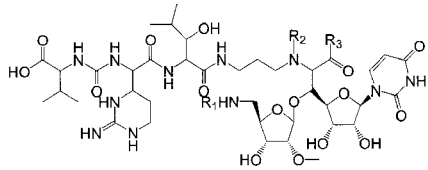

"

<u>Column 36,</u>
Lines 5-25, delete the structure

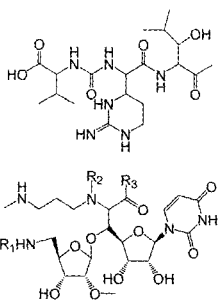   and insert the structure   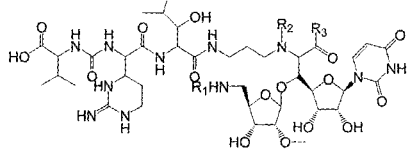

UNITED STATES PATENT AND TRADEMARK OFFICE
CERTIFICATE OF CORRECTION

PATENT NO.     : 6,727,232 B2
DATED          : April 27, 2004
INVENTOR(S)    : Yang-I Lin et al.

It is certified that error appears in the above-identified patent and that said Letters Patent is hereby corrected as shown below:

Column 37,
Line 51, please delete
"
       dioxo-3,4-dihydro
                        " and insert
-- (Aminomethyl)-4-hydroxy-3-methoxytetrahydro-2-furanyl]oxy} {(2S,3S,4R.5R)-5-[2,4-dioxo-3,4-dihydro- -- therefore.

Column 40,
Lines 8-34, delete the structures

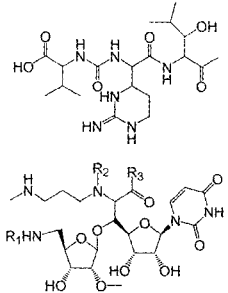 and insert the structure 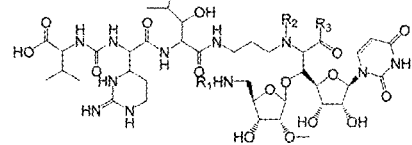

Lines 44-66, delete the structure

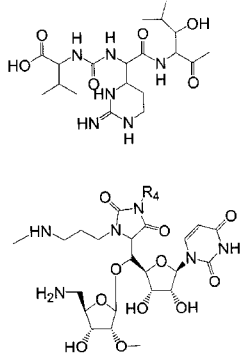 and insert the structure 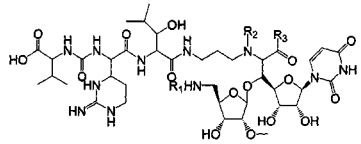

UNITED STATES PATENT AND TRADEMARK OFFICE
CERTIFICATE OF CORRECTION

PATENT NO. : 6,727,232 B2
DATED : April 27, 2004
INVENTOR(S) : Yang-I Lin et al.

Page 3 of 3

It is certified that error appears in the above-identified patent and that said Letters Patent is hereby corrected as shown below:

Column 41,
Lines 10-36, delete the structures

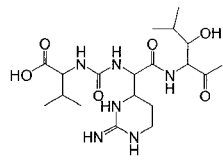 and insert the structure 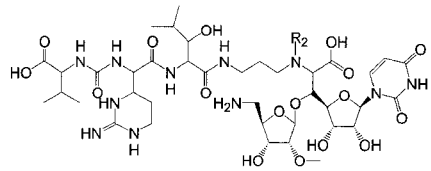

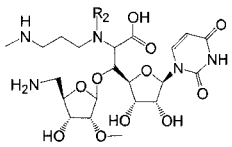

Column 42,
Lines 5-27, delete the structures

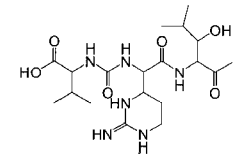 and insert the structure 

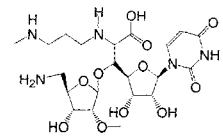

Signed and Sealed this

Seventh Day of September, 2004

JON W. DUDAS
*Director of the United States Patent and Trademark Office*